United States Patent
Koike

(10) Patent No.: US 12,417,565 B2
(45) Date of Patent: Sep. 16, 2025

(54) IMAGE GENERATION DEVICE, IMAGE GENERATION PROGRAM, LEARNING DEVICE, LEARNING PROGRAM, IMAGE PROCESSING DEVICE, AND IMAGE PROCESSING PROGRAM

(71) Applicant: FUJIFILM CORPORATION, Tokyo (JP)

(72) Inventor: Takafumi Koike, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 566 days.

(21) Appl. No.: 17/818,362

(22) Filed: Aug. 9, 2022

(65) Prior Publication Data

US 2022/0383564 A1    Dec. 1, 2022

Related U.S. Application Data

(63) Continuation of application No. PCT/JP2021/008162, filed on Mar. 3, 2021.

(30) Foreign Application Priority Data

Mar. 13, 2020  (JP) ................. 2020-044697

(51) Int. Cl.
*A61B 6/00* (2024.01)
*G06T 7/00* (2017.01)
(Continued)

(52) U.S. Cl.
CPC .......... *G06T 11/003* (2013.01); *G06T 7/0012* (2013.01); *G06T 7/344* (2017.01);
(Continued)

(58) Field of Classification Search
CPC ..... G06T 11/003; G06T 7/0012; G06T 7/344; G06T 2207/10124; G06T 2207/20081;
(Continued)

(56) References Cited

U.S. PATENT DOCUMENTS 9,792,703 B2    10/2017  Costa et al.
2004/0101095 A1  5/2004  Jing et al.
(Continued)

FOREIGN PATENT DOCUMENTS

JP  2007-283108 A  11/2007
JP  2008-048880 A   3/2008
(Continued)

OTHER PUBLICATIONS

Eman Shaheen et al., "The simulation of 3D microcalcification clusters in 2D digital mammography and breast tomosynthesis", Medical Physics, AIP, Melville, NY, US, vol. 38, No. 12, Dec. 1, 2011, pp. 6659-6671.
(Continued)

*Primary Examiner* — Cindy Trandai
(74) *Attorney, Agent, or Firm* — SOLARIS Intellectual Property Group, PLLC

(57) ABSTRACT

A processor acquires a plurality of first projection images acquired by imaging an object at a plurality of radiation source positions and acquires a lesion image indicating a lesion. The processor combines the lesion image with the plurality of first projection images on the basis of a geometrical relationship between the plurality of radiation source positions and a position of the lesion virtually disposed in the object to derive a plurality of second projection images. The processor reconstructs the plurality of second projection images to generate a tomographic image including the lesion.

17 Claims, 16 Drawing Sheets

(51) Int. Cl.
*G06T 7/33* (2017.01)
*G06T 11/00* (2006.01)

(52) U.S. Cl.
CPC ........... *G06T 2207/10124* (2013.01); *G06T 2207/20081* (2013.01); *G06T 2207/30096* (2013.01)

(58) Field of Classification Search
CPC ..... G06T 2207/30096; G06T 2211/441; G06T 11/006; G06T 2211/436; G06N 3/044; G06N 3/09; G06N 3/0464; G06N 3/047; A61B 6/502; A61B 6/5217; A61B 6/0414; A61B 6/02; A61B 6/00
See application file for complete search history.

(56) References Cited

U.S. PATENT DOCUMENTS

| | | |
|---|---|---|
| 2005/0113681 A1 | 5/2005 | Defreitas et al. |
| 2006/0098855 A1 | 5/2006 | Gkanatsios et al. |
| 2007/0030949 A1 | 2/2007 | Jing et al. |
| 2007/0242901 A1 | 10/2007 | Huang et al. |
| 2008/0019581 A1 | 1/2008 | Gkanatsios et al. |
| 2008/0130979 A1 | 6/2008 | Ren et al. |
| 2008/0232667 A1 | 9/2008 | Kitamura et al. |
| 2009/0003519 A1 | 1/2009 | Defreitas et al. |
| 2009/0010384 A1 | 1/2009 | Jing et al. |
| 2009/0123052 A1 | 5/2009 | Ruth et al. |
| 2009/0141859 A1 | 6/2009 | Gkanatsios et al. |
| 2009/0213987 A1 | 8/2009 | Stein et al. |
| 2009/0268865 A1 | 10/2009 | Ren et al. |
| 2009/0296882 A1 | 12/2009 | Gkanatsios et al. |
| 2010/0135456 A1 | 6/2010 | Jing et al. |
| 2010/0135558 A1 | 6/2010 | Ruth et al. |
| 2010/0195882 A1 | 8/2010 | Ren et al. |
| 2011/0069808 A1 | 3/2011 | Defreitas et al. |
| 2011/0069809 A1 | 3/2011 | Defreitas et al. |
| 2011/0135185 A1 | 6/2011 | Gkanatsios et al. |
| 2011/0216879 A1 | 9/2011 | Jing et al. |
| 2012/0195484 A1 | 8/2012 | Ren et al. |
| 2012/0219111 A1 | 8/2012 | Defreitas et al. |
| 2013/0028374 A1 | 1/2013 | Gkanatsios et al. |
| 2013/0223591 A1 | 8/2013 | Jing et al. |
| 2013/0272494 A1 | 10/2013 | Defreitas et al. |
| 2014/0044230 A1 | 2/2014 | Stein et al. |
| 2014/0044231 A1 | 2/2014 | Defreitas et al. |
| 2014/0086471 A1 | 3/2014 | Ruth et al. |
| 2014/0232752 A1 | 8/2014 | Ren et al. |
| 2014/0301529 A1 | 10/2014 | Ren et al. |
| 2014/0327702 A1 | 11/2014 | Kreeger et al. |
| 2014/0376690 A1 | 12/2014 | Jing et al. |
| 2015/0049859 A1 | 2/2015 | Defreitas et al. |
| 2015/0160848 A1 | 6/2015 | Gkanatsios et al. |
| 2015/0182181 A1 | 7/2015 | Ruth et al. |
| 2015/0310611 A1 | 10/2015 | Gkanatsios et al. |
| 2015/0317538 A1 | 11/2015 | Ren et al. |
| 2016/0189376 A1* | 6/2016 | Bernard ................ A61B 6/502 382/132 |
| 2016/0220210 A1 | 8/2016 | Ruth et al. |
| 2017/0024113 A1 | 1/2017 | Gkanatsios et al. |
| 2017/0128028 A1 | 5/2017 | Defreitas et al. |
| 2017/0135650 A1 | 5/2017 | Stein et al. |
| 2017/0236276 A1* | 8/2017 | Fukuda ................ G06T 11/003 382/131 |
| 2017/0337682 A1* | 11/2017 | Liao ........................ G06T 7/30 |
| 2018/0012398 A1* | 1/2018 | Baumgart ............ A61B 6/487 |
| 2018/0055470 A1 | 3/2018 | Ruth et al. |
| 2018/0137385 A1 | 5/2018 | Ren et al. |
| 2018/0177476 A1 | 6/2018 | Jing et al. |
| 2018/0188937 A1 | 7/2018 | Gkanatsios et al. |
| 2018/0289347 A1 | 10/2018 | Defreitas et al. |
| 2018/0325489 A1* | 11/2018 | De Beni ............ A61B 5/0035 |
| 2018/0344276 A1 | 12/2018 | Defreitas et al. |
| 2019/0000318 A1* | 1/2019 | Caluser ............... A61B 5/0073 |
| 2019/0043456 A1 | 2/2019 | Kreeger et al. |
| 2019/0053776 A1 | 2/2019 | Ruth et al. |
| 2019/0095087 A1 | 3/2019 | Gkanatsios et al. |
| 2019/0096098 A1* | 3/2019 | Fukuda ................ G06T 11/006 |
| 2019/0200942 A1 | 7/2019 | Defreitas et al. |
| 2019/0221010 A1* | 7/2019 | Fukuda ................ A61B 6/025 |
| 2019/0282183 A1* | 9/2019 | Armand ............... A61B 90/36 |
| 2019/0325255 A1 | 10/2019 | Ren et al. |
| 2020/0012417 A1 | 1/2020 | Gkanatsios et al. |
| 2020/0020140 A1* | 1/2020 | Maltz ................... G06T 11/006 |
| 2020/0022663 A1 | 1/2020 | Ren et al. |
| 2020/0258479 A1 | 8/2020 | Kreeger et al. |
| 2020/0348835 A1 | 11/2020 | Gkanatsios et al. |
| 2021/0042917 A1* | 2/2021 | Hirai .................... G06V 10/751 |
| 2021/0128807 A1 | 5/2021 | Defreitas et al. |
| 2021/0204894 A1 | 7/2021 | Ren et al. |
| 2021/0212795 A1* | 7/2021 | Zupon ................... A61B 8/483 |
| 2021/0259649 A1* | 8/2021 | Milioni De Carvalho ................. G06T 7/337 |
| 2022/0013089 A1 | 1/2022 | Kreeger et al. |
| 2022/0015731 A1* | 1/2022 | Liu ....................... A61B 6/502 |
| 2022/0071582 A1 | 3/2022 | Defreitas et al. |

FOREIGN PATENT DOCUMENTS

| | | |
|---|---|---|
| JP | 2008-229161 A | 10/2008 |
| JP | 2014-128716 A | 7/2014 |
| JP | 2020-018705 A | 2/2020 |
| WO | 2017/221537 A1 | 12/2017 |

OTHER PUBLICATIONS

Kenji Suzuki et al., "Massive-training artificial neural network (MTANN) for reduction of false positives in computer-aided detection of polyps:Suppression of rectal tubes", Medical Physics, AIP, Melville, NY, US, vol. 33, No. 10, Sep. 25, 2006, pp. 3814-3824.
Extended European Search Report dated Jul. 6, 2023, issued in corresponding EP Patent Application No. 21766927.4.
English language translation of the following: Office action dated Sep. 19, 2023 from the JPO in a Japanese patent application No. 2022-505970 corresponding to the instant patent application.
Kazuya Abe et al., "Making of New Artificially Calcified Shadow for Breast Cancer and Effective Inspection of the CAD development Technique Not to Use A True Case at All", Medical Imaging Technology, 2017, vol. 35, No. 5, pp. 268-272, entire text, all drawings.
Hui Li et al., "Deep learning in breast cancer risk assessment: evaluation of convolutional neural networks on a clinical dataset of full-field digital mammograms", Journal of Medical Imaging, 2017, vol. 4 (4), 041304, 041304-1 to 041304-6, entire text, all drawings.
International Search Report issued in International Application No. PCT/JP2021/008162 on Apr. 27, 2021.
Written Opinion of the ISA issued in International Application No. PCT/JP2021/008162 on Apr. 27, 2021.

* cited by examiner

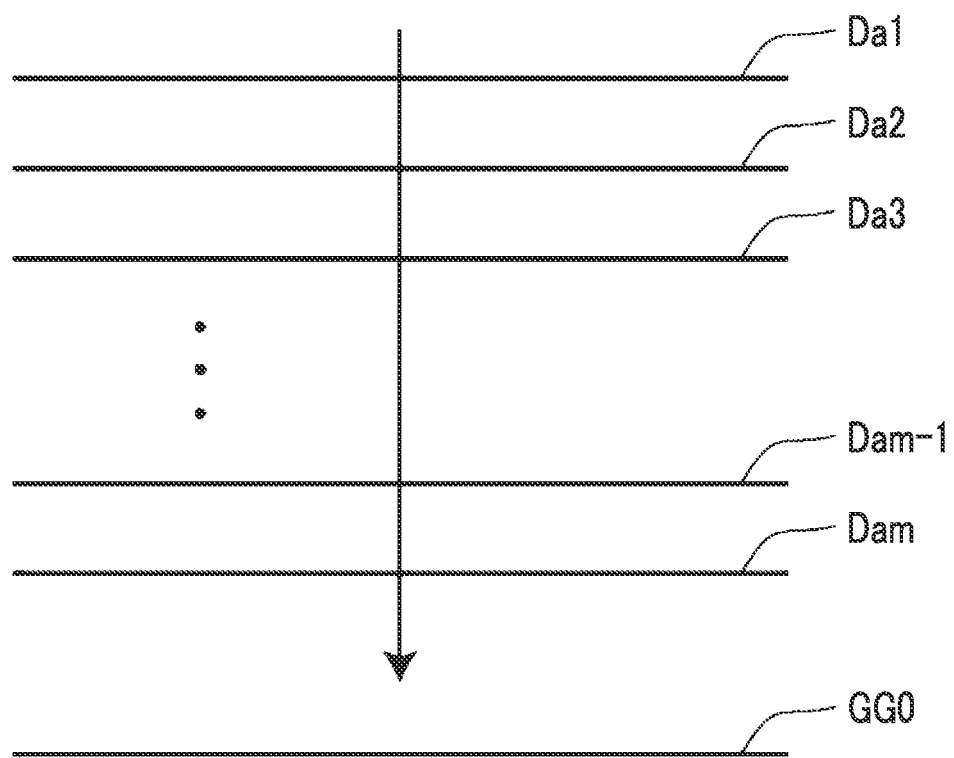

IMAGE GENERATION DEVICE, IMAGE GENERATION PROGRAM, LEARNING DEVICE, LEARNING PROGRAM, IMAGE PROCESSING DEVICE, AND IMAGE PROCESSING PROGRAM

CROSS REFERENCE TO RELATED APPLICATIONS

The present application is a Continuation of PCT International Application No. PCT/JP2021/008162, filed on Mar. 3, 2021, which claims priority to Japanese Patent Application No. 2020-044697, filed on Mar. 13, 2020. Each application above is hereby expressly incorporated by reference, in its entirety, into the present application.

BACKGROUND

Technical Field

The present disclosure relates to an image generation device, an image generation program, a learning device, a learning program, an image processing device, and an image processing program.

Related Art

In recent years, image diagnosis using a radiography apparatus (called mammography) for capturing an image of a breast has attracted attention in order to promote early detection of breast cancer. Further, in the mammography, tomosynthesis imaging has been proposed which moves a radiation source, irradiates the breast with radiation at a plurality of radiation source positions to acquire a plurality of projection images, and reconstructs the plurality of acquired projection images to generate tomographic images in which desired tomographic planes have been highlighted. In the tomosynthesis imaging, the radiation source is moved in parallel to a radiation detector or is moved so as to draw a circular or elliptical arc according to the characteristics of an imaging apparatus and the required tomographic image, and imaging is performed on the breast at a plurality of radiation source positions to acquire a plurality of projection images. Then, the projection images are reconstructed using, for example, a back projection method, such as a simple back projection method or a filtered back projection method, or a sequential reconstruction method to generate tomographic images.

The tomographic images are generated in a plurality of tomographic planes of the breast, which makes it possible to separate structures that overlap each other in a depth direction in which the tomographic planes are arranged in the breast. Therefore, it is possible to find an abnormal part such as a lesion that has been difficult to detect in a two-dimensional image (hereinafter, referred to as a simple two-dimensional image) acquired by simple imaging according to the related art which irradiates an object with radiation in a predetermined direction.

Meanwhile, in a medical field, a computer-aided diagnosis (hereinafter, referred to as CAD) system is known which automatically detects a lesion in an image using a learning model which is a machine learning model, such as a neural network trained by deep learning or the like, and displays the detected lesion so as to be highlighted. For example, the CAD is used to detect lesions, such as a calcification, a spicula, and a tumor, from the tomographic images acquired by the tomosynthesis imaging.

However, it is necessary to train the machine learning model, using a training image including a lesion and information indicating the position of the lesion in the training image as training data, in order to construct the machine learning model in the CAD. In particular, it is necessary to prepare a large amount of training data in order to improve the accuracy of detection. However, it is not easy to prepare a large number of training images including lesions.

Therefore, a method has been proposed that artificially adds a lesion image to a normal image, which does not include a lesion, to generate a training image including the lesion and constructs a learning model using the training image including the lesion and the normal image as training data (see JP2008-229161A).

However, the training image including the lesion generated by the method disclosed in JP2008-229161A is generated by adding the image of the lesion to a two-dimensional image captured by simple imaging. Therefore, even in a case in which the method disclosed in JP2008-229161A is applied to the projection image acquired by the tomosynthesis imaging without any change, it is not possible to derive a tomographic image including the lesion with high accuracy. Further, even in a case in which the machine learning model trained using the tomographic image as the training image is used, it may not be possible to detect the lesion from the image with high accuracy.

Furthermore, the method disclosed in JP2008-229161A simply combines the lesion image with the normal image. Therefore, the generated training image including the lesion looks different from the image actually acquired by the imaging apparatus. As a result, in a case in which the machine learning model is constructed using the training image, it may not be possible to detect the lesion from the image with high accuracy.

SUMMARY OF THE INVENTION

The present invention has been made in view of the above circumstances, and an object of the present invention is to provide a technique that can detect a lesion from an image with high accuracy.

A first image generation device according to the present disclosure comprises at least one processor. The processor is configured to acquire a plurality of first projection images acquired by imaging an object at a plurality of radiation source positions, to acquire a lesion image indicating a lesion, to combine the lesion image with the plurality of first projection images on the basis of a geometrical relationship between the plurality of radiation source positions and a position of the lesion virtually disposed in the object to derive a plurality of second projection images, and to reconstruct the plurality of second projection images to generate a tomographic image including the lesion.

In addition, in the first image generation device according to the present disclosure, the processor may be configured to derive a radiation attenuation coefficient for the lesion virtually disposed in the object and to derive the plurality of second projection images on the basis of the radiation attenuation coefficient.

Further, in the first image generation device according to the present disclosure, the processor may generate training data that includes the tomographic image including the lesion and data indicating a position of the lesion in the tomographic image including the lesion and that is used to perform machine learning on a model for detecting the lesion included in a target image in a case in which the target image is input.

A second image generation device according to the present disclosure comprises at least one processor. The processor is configured to acquire an image acquired by performing radiography on an object, to acquire a lesion image indicating a lesion, to derive a radiation attenuation coefficient for the lesion virtually disposed in the object, and to combine the lesion image with the image on the basis of the radiation attenuation coefficient and a geometrical relationship between a radiation source position in a case in which the radiography is performed and a position of the lesion virtually disposed in the object to generate an image.

Further, in the second image generation device according to the present disclosure, the processor may generate training data that includes the image in which the lesion image has been combined and data indicating a position of the lesion in the image in which the lesion image has been combined and that is used to perform machine learning on a model for detecting the lesion included in a target image in a case in which the target image is input.

Furthermore, in the first and second image generation devices according to the present disclosure, the lesion may be at least one of a tumor, a spicula or a calcification.

A learning device according to the present disclosure comprises at least one processor. The processor is configured to construct a model, which detects a lesion included in a target image in a case in which the target image is input, with machine learning, using first training data which is the training data generated by the first and second image generation devices according to the present disclosure and second training data which is an image that does not include the lesion.

An image processing device according to the present disclosure comprises: at least one processor; and the model constructed by the learning device according to the present disclosure. The processor is configured to acquire a target image and to detect a lesion included in the target image using the model.

Moreover, in the image processing device according to the present disclosure, the processor may be configured to display a detection result of the lesion.

A first image generation program according to the present disclosure causes a computer to execute: a procedure of acquiring a plurality of first projection images acquired by imaging an object at a plurality of radiation source positions; a procedure of acquiring a lesion image indicating a lesion; a procedure of combining the lesion image with the plurality of first projection images on the basis of a geometrical relationship between the plurality of radiation source positions and a position of the lesion virtually disposed in the object to derive a plurality of second projection images; and a procedure of reconstructing the plurality of second projection images to generate a tomographic image including the lesion.

A second image generation program according to the present disclosure causes a computer to execute: a procedure of acquiring an image acquired by performing radiography on an object; a procedure of acquiring a lesion image indicating a lesion; a procedure of deriving a radiation attenuation coefficient for the lesion virtually disposed in the object; and a procedure of combining the lesion image with the image on the basis of the radiation attenuation coefficient and a geometrical relationship between a radiation source position in a case in which the radiography is performed and a position of the lesion virtually disposed in the object to generate an image.

A learning program according to the present disclosure causes a computer to execute a procedure of constructing a model, which detects a lesion included in a target image in a case in which the target image is input, with machine learning, using first training data which is the training data generated by the first and second image generation devices according to the present disclosure and second training data which is an image that does not include the lesion.

An image processing program according to the present disclosure causes a computer to execute: a procedure of acquiring a target image; and a procedure of detecting a lesion included in the target image using the model constructed by the learning device according to the present disclosure.

According to the present disclosure, it is possible to detect a lesion from an image with high accuracy.

BRIEF DESCRIPTION OF THE DRAWINGS

FIG. 22 is a diagram illustrating the generation of a composite two-dimensional image.

DESCRIPTION OF THE PREFERRED EMBODIMENTS

Figure 1:
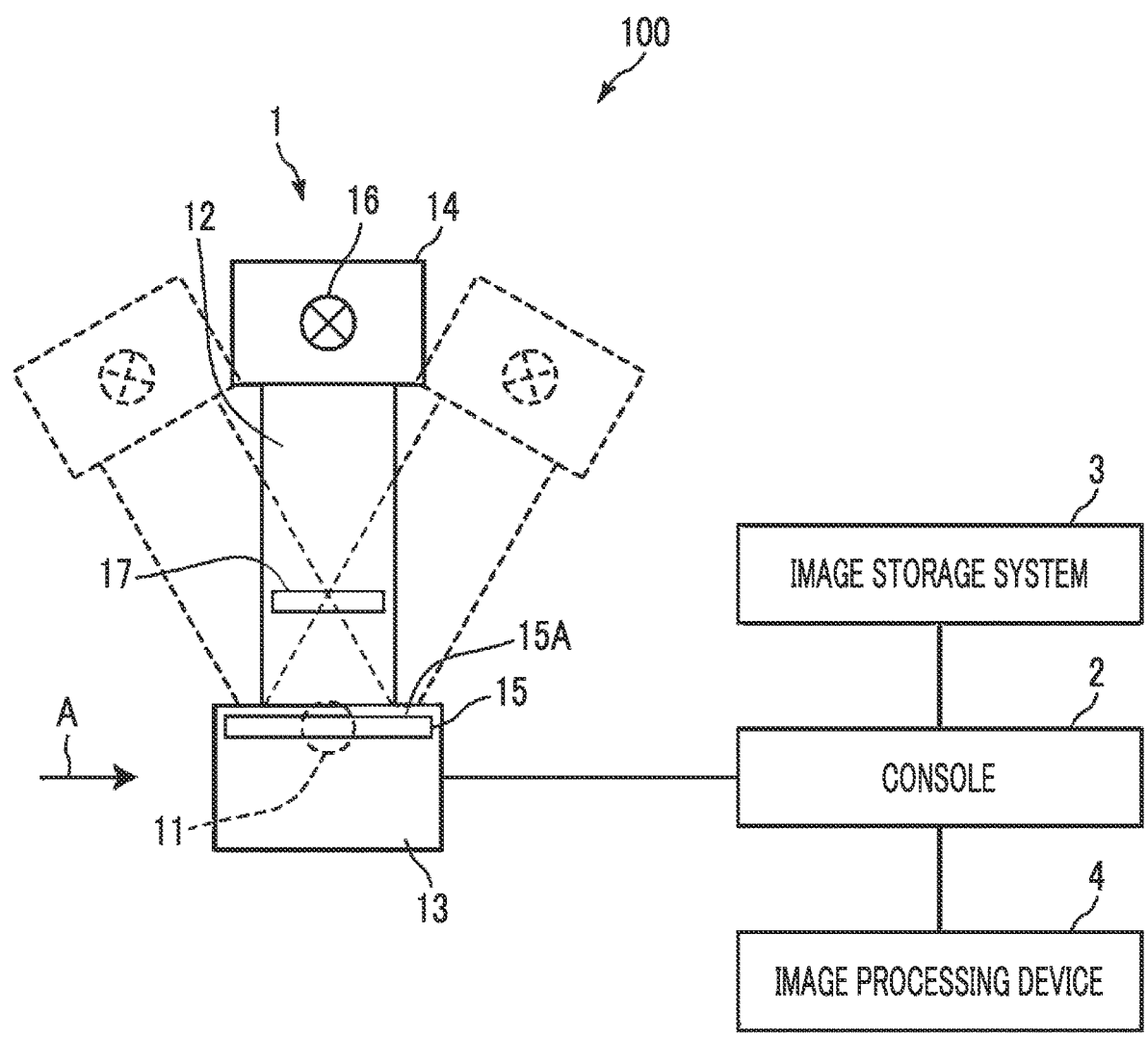
FIG. 1 is a diagram schematically illustrating a configuration of a radiography system to which an image processing device according to a first embodiment of the present disclosure is applied.
Figure 2:
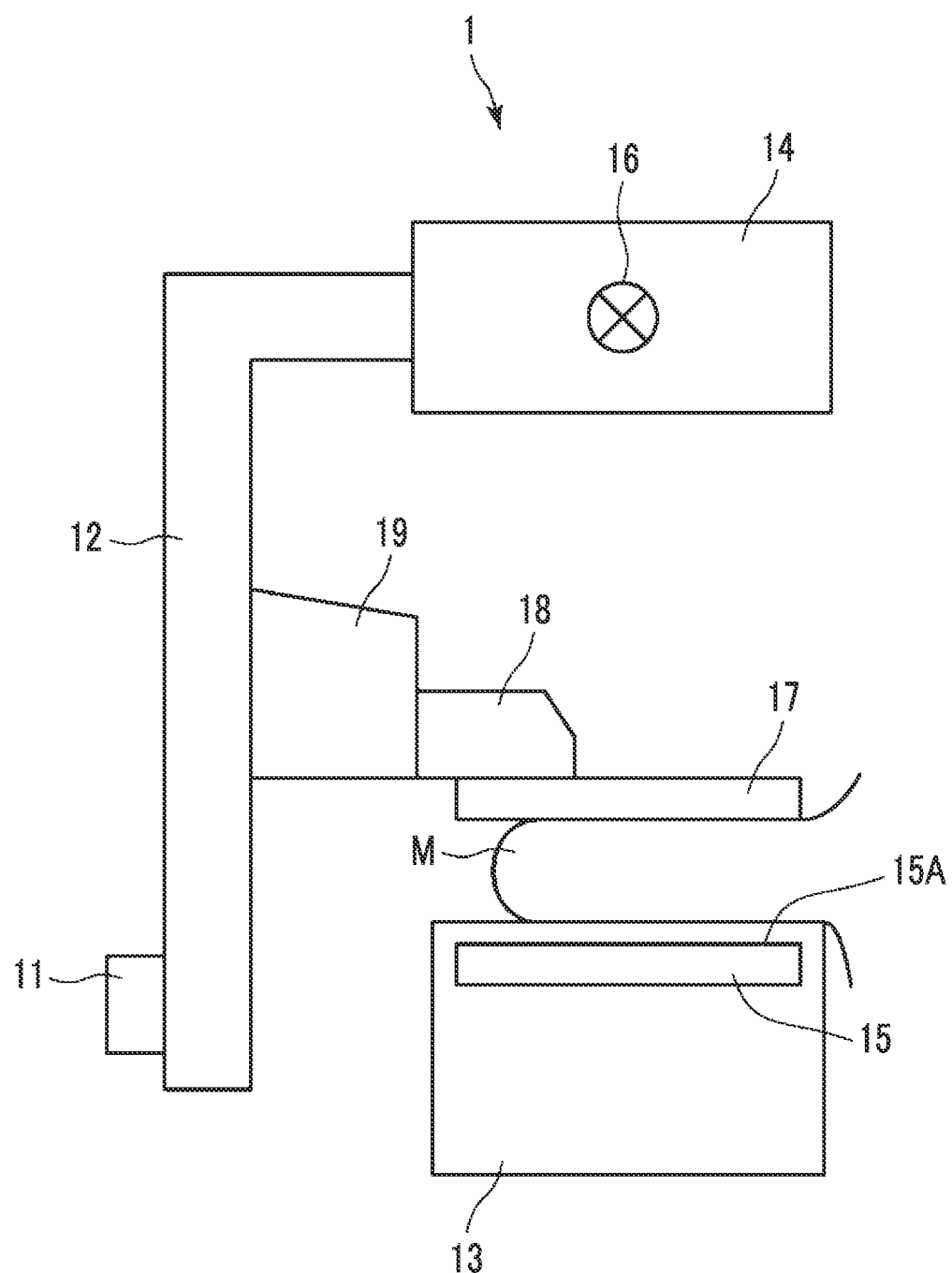
FIG. 2 is a diagram illustrating a radiography apparatus as viewed from a direction of an arrow A in FIG. 1.

Hereinafter, embodiments of the present disclosure will be described with reference to the drawings. FIG. 1 is a diagram schematically illustrating a configuration of a radiography system to which an image processing device according to a first embodiment of the present disclosure is applied, and FIG. 2 is a diagram illustrating a mammography apparatus in the radiography system as viewed from a direction of an arrow A in FIG. 1. As illustrated in FIG. 1, a radiography system 100 according to this embodiment comprises a mammography apparatus 1, a console 2, an image storage system 3, and an image processing device 4. The mammography apparatus 1 images a breast M, which is an object, at a plurality of radiation source positions and acquires a plurality of radiographic images, that is, a plurality of projection images, in order to perform tomosynthesis imaging on the breast to generate tomographic images. In addition, the mammography apparatus 1 can also perform simple imaging that irradiates the breast M with radiation at a predetermined radiation source position to acquire a two-dimensional radiographic image of the breast.

The mammography apparatus 1 comprises an arm portion 12 that is connected to a base (not illustrated) by a rotation shaft 11. An imaging table 13 is attached to one end of the arm portion 12, and a radiation emitting unit 14 is attached to the other end of the arm portion 12 so as to face the imaging table 13. The arm portion 12 is configured such that only the end to which the radiation emitting unit 14 is attached can be rotated. Therefore, the imaging table 13 is fixed, and only the radiation emitting unit 14 can be rotated.

A radiation detector 15, such as a flat panel detector, is provided in the imaging table 13. The radiation detector 15 has a detection surface 15A for radiation. In addition, for example, a circuit substrate including a charge amplifier that converts a charge signal read from the radiation detector 15 into a voltage signal, a correlated double sampling circuit that samples the voltage signal output from the charge amplifier, and an analog-digital (AD) conversion unit that converts the voltage signal into a digital signal is provided in the imaging table 13.

A radiation source 16 is accommodated in the radiation emitting unit 14. The radiation source 16 emits, for example, X-rays as the radiation. The console 2 controls the timing when the radiation source 16 emits the radiation and the radiation generation conditions of the radiation source 16, that is, the selection of target and filter materials, a tube voltage, an irradiation time, and the like.

Further, the arm portion 12 is provided with a compression plate 17 that is disposed above the imaging table 13 and presses and compresses the breast M, a support portion 18 that supports the compression plate 17, and a movement mechanism 19 that moves the support portion 18 in an up-down direction in FIGS. 1 and 2. In addition, an interval between the compression plate 17 and the imaging table 13, that is, a compression thickness is input to the console 2.

The console 2 has a function of controlling the mammography apparatus 1 using, for example, an imaging order and various kinds of information acquired from a radiology information system (RIS) (not illustrated) or the like through a network, such as a wireless communication local area network (LAN), and instructions or the like directly issued by a radiology technician or the like. Specifically, the console 2 directs the mammography apparatus 1 to perform the tomosynthesis imaging on the breast M to acquire a plurality of projection images as described below. For example, in this embodiment, a server computer is used as the console 2.

The image storage system 3 is a system that stores image data such as radiographic images, projection images, and tomographic images captured by the mammography apparatus 1. The image storage system 3 extracts an image corresponding to a request from, for example, the console 2 and the image processing device 4 from the stored images and transmits the image to a device that is the source of the request. A specific example of the image storage system 3 is a picture archiving and communication system (PACS).

Figure 3:
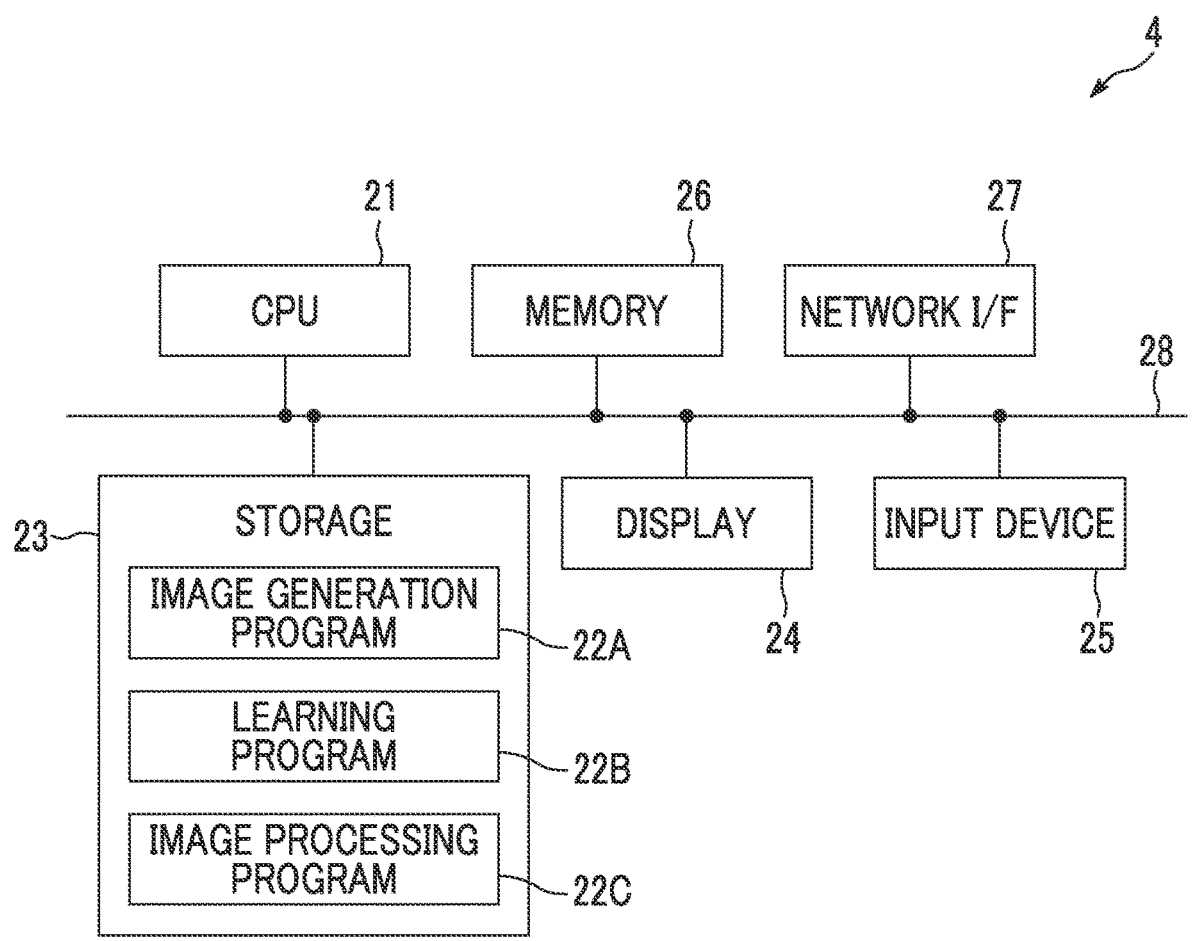
FIG. 3 is a diagram schematically illustrating a configuration of the image processing device according to the first embodiment.

Next, the image processing device according to the first embodiment will be described. In addition, the image processing device 4 according to the first embodiment includes an image generation device and a learning device according to the present disclosure. However, in the following description, it is assumed that the image processing device represents the devices. Next, a hardware configuration of the image processing device according to the first embodiment will be described with reference to FIG. 3. As illustrated in FIG. 3, the image processing device 4 is a computer, such as a workstation, a server computer, or a personal computer, and comprises a central processing unit (CPU) 21, a non-volatile storage 23, and a memory 26 as a temporary storage area. In addition, the image processing device 4 comprises a display 24, such as a liquid crystal display, an input device 25, such as a keyboard and a mouse, and a network interface (I/F) 27 that is connected to a network (not illustrated). The CPU 21, the storage 23, the display 24, the input device 25, the memory 26, and the network I/F 27 are connected to a bus 28. In addition, the CPU 21 is an example of a processor according to the present disclosure.

The storage 23 is implemented by, for example, a hard disk drive (HDD), a solid state drive (SSD), and a flash memory. The storage 23 as a storage medium stores an image generation program 22A, a learning program 22B, and an image processing program 22C which are installed in the image processing device 4. The CPU 21 reads the image generation program 22A, the learning program 22B, and the image processing program 22C from the storage 23, expands the programs in the memory 26, and executes the expanded image generation program 22A, learning program 22B, and image processing program 22C.

In addition, the image generation program 22A, the learning program 22B, and the image processing program 22C are stored in a storage device of a server computer connected to the network or a network storage so as to be accessed from the outside and are downloaded and installed in the computer constituting the image processing device 4 on demand. Alternatively, the programs are recorded on a recording medium, such as a digital versatile disc (DVD) or a compact disc read only memory (CD-ROM), are distributed, and are installed in the computer constituting the image processing device 4 from the recording medium.

Figure 4:
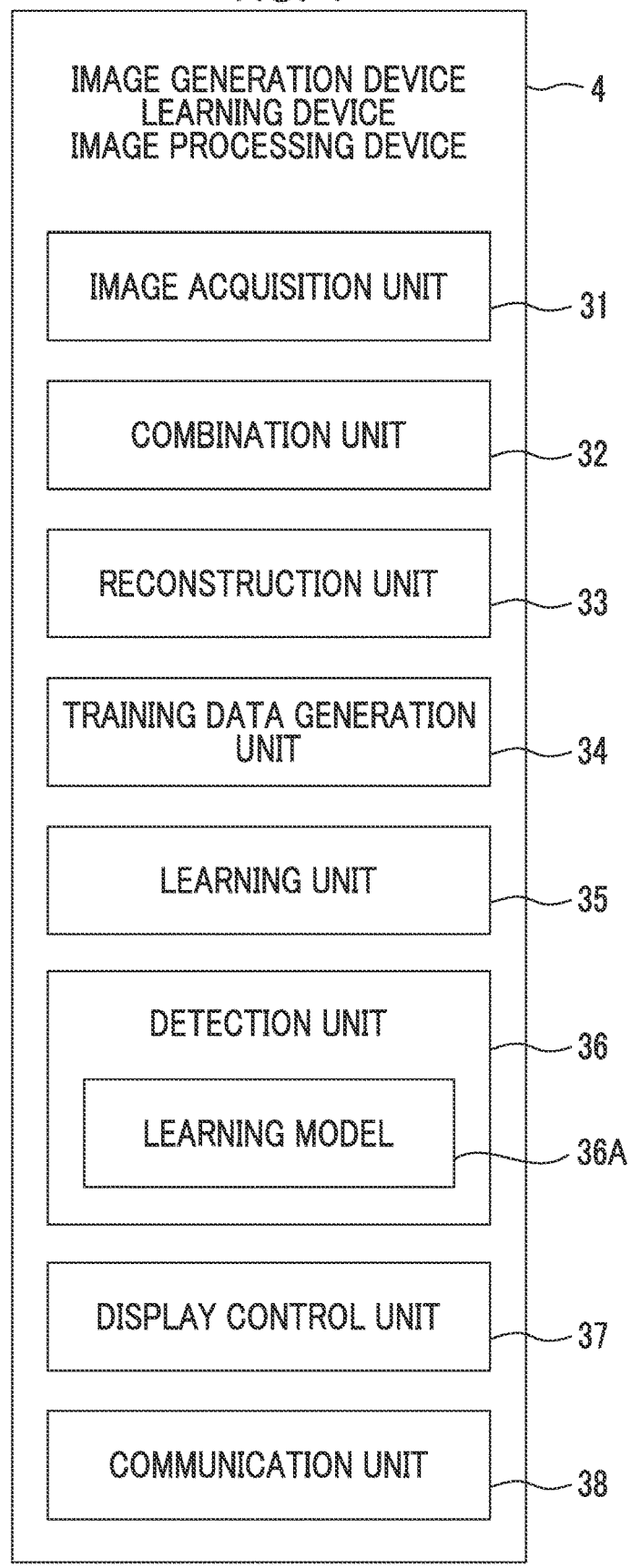
FIG. 4 is a diagram illustrating a functional configuration of the image processing device according to the first embodiment.

Next, a functional configuration of the image processing device according to the first embodiment will be described. FIG. 4 is a diagram illustrating the functional configuration of the image processing device according to the first embodiment. As illustrated in FIG. 4, the image processing device 4 comprises an image acquisition unit 31, a combination unit 32, a reconstruction unit 33, a training data generation unit 34, a learning unit 35, a detection unit 36, a display control unit 37, and a communication unit 38. Then, the CPU 21 executes the image generation program 22A, the learning program 22B, and the image processing program 22C such that the image processing device 4 functions as the image acquisition unit 31, the combination unit 32, the reconstruction unit 33, the training data generation unit 34, the learning unit 35, the detection unit 36, the display control unit 37, and the communication unit 38. In addition, a learning model 36A, which will be described later, is applied to the detection unit 36.

In addition, for example, the image acquisition unit 31, the combination unit 32, the reconstruction unit 33, the training data generation unit 34, the display control unit 37, and the communication unit 38 constitute the image generation device according to the first embodiment. Further, for example, the image acquisition unit 31 and the learning unit 35 constitute the learning device according to the first embodiment. Furthermore, for example, the image acquisition unit 31, the detection unit 36, and the display control unit 37 constitute the image processing device according to the first embodiment.

The image acquisition unit 31 acquires a plurality of projection images acquired by the tomosynthesis imaging performed by the mammography apparatus 1 under the control of the console 2. In addition, the image acquisition unit 31 acquires a lesion image of a simulated lesion schematically indicating a lesion included in the breast M. The image acquisition unit 31 acquires the projection image from the console 2 or the image storage system 3 through the network I/F 27. Further, the image acquisition unit 31 acquires the lesion image from the image storage system 3 through the network I/F 27. Furthermore, the image acquisition unit 31 acquires the training data, which has been generated as described below and stored in the image storage system 3, through the network I/F 27 in order to train a learning model which will be described below. Moreover, the image acquisition unit 31 acquires a target image, from which a lesion is to be detected as described below, from the image storage system 3 through the network I/F 27.

Here, the tomosynthesis imaging in the console 2 will be described. In a case in which the tomosynthesis imaging for generating tomographic images is performed, the console 2 rotates the arm portion 12 about the rotation shaft 11 to move the radiation source 16, irradiates the breast M, which is an object, with radiation at a plurality of radiation source positions caused by the movement of the radiation source 16 under predetermined imaging conditions for tomosynthesis imaging, detects the radiation transmitted through the breast M using the radiation detector 15, and acquires a plurality of projection images Gi (i=1 to n, where n is the number of radiation source positions and is, for example, 15) at the plurality of radiation source positions.

Figure 5:
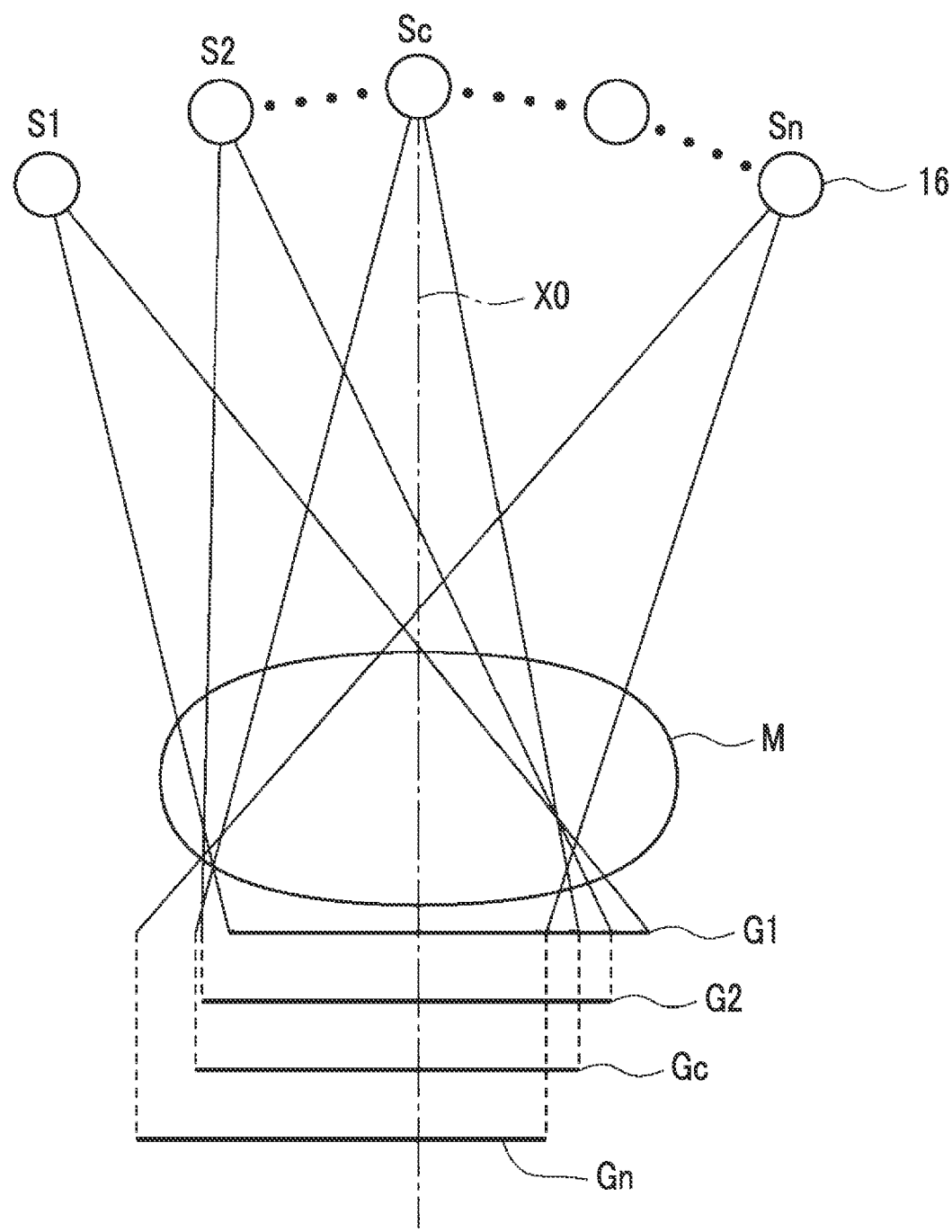
FIG. 5 is a diagram illustrating the acquisition of projection images.

FIG. 5 is a diagram illustrating the acquisition of the projection images Gi. As illustrated in FIG. 5, the radiation source 16 is moved to each of radiation source positions S1, S2, . . . , and Sn. The radiation source 16 is driven at each radiation source position to irradiate the breast M with radiation. The radiation detector 15 detects the X-rays transmitted through the breast M to acquire projection images G1, G2, . . . , and Gn corresponding to the radiation source positions S1 to Sn, respectively. In addition, at each of the radiation source positions S1 to Sn, the breast M is irradiated with the same dose of radiation. Further, in the following description, it is assumed that the projection image Gi is referred to as a first projection image.

Furthermore, in FIG. 5, a radiation source position Sc is a radiation source position where an optical axis X0 of the radiation emitted from the radiation source 16 is orthogonal to the detection surface 15A of the radiation detector 15. It is assumed that the radiation source position Sc is referred to as a reference radiation source position Sc.

The combination unit 32 combines the lesion image of the simulated lesion with a plurality of first projection images Gi on the basis of a geometrical relationship between a plurality of radiation source positions in a case in which the mammography apparatus 1 performs the tomosynthesis imaging and the position of the lesion disposed at a predetermined position in the breast M to derive a plurality of second projection images. In addition, examples of the type of lesion in the breast M include a tumor, a spicula, and a calcification.

Figures 6, 7:
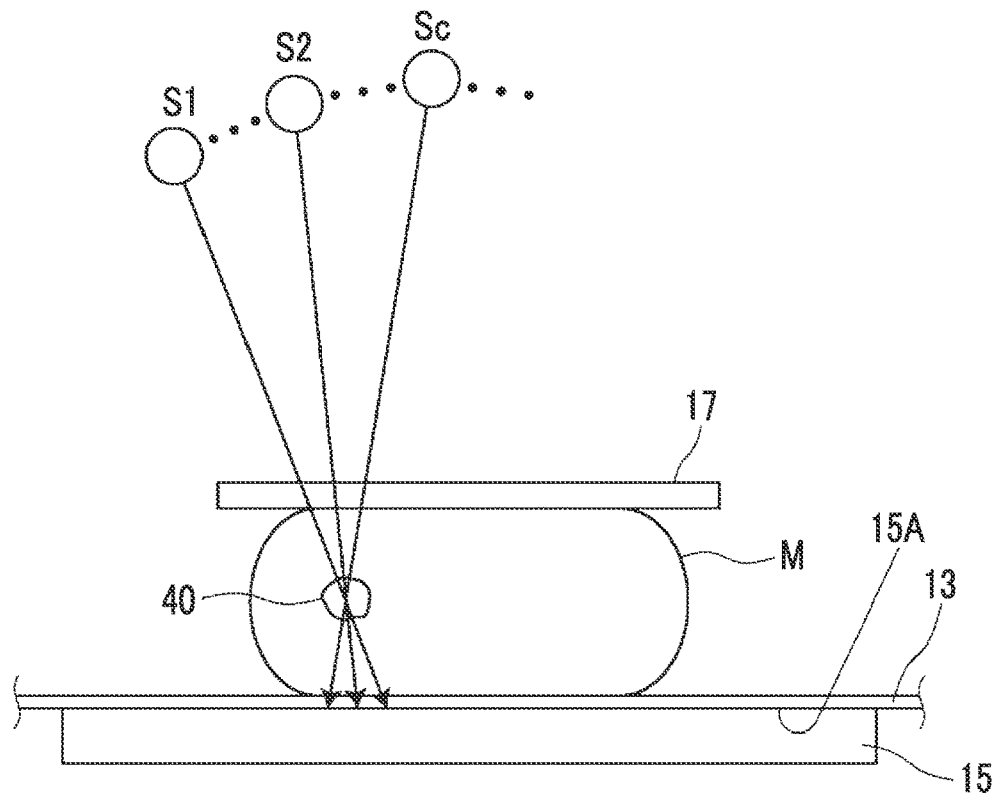
FIG. 6 is a diagram illustrating lesion images of simulated lesions for various types of lesions.
FIG. 7 is a diagram illustrating the derivation of a combination position of the lesion image in the first embodiment.

FIG. 6 is a diagram illustrating lesion images of simulated lesions for various lesions. As illustrated in FIG. 6, an image similar to the shape of an actual lesion is prepared as the lesion image of the simulated lesion. Specifically, the images of a sphere, an ellipsoid, a polygon, a lobulated shape, and an irregular shape are prepared as the lesion images of the tumors. In addition, the images of a tumor accompanied by a spicula and a disordered construction are prepared as the lesion images of the spiculae. The disordered construction indicates a state without a tumor. In addition, the images of a sphere, a polygon, a line, and a lobulated shape are prepared as the lesion images of the calcifications.

Further, the lesion image of the simulated lesion may be obtained by performing radiography on the breast including the actual lesion or may be artificially generated by computer graphics or the like. In this embodiment, the lesion image generated by computer graphics is used.

Figure 8:
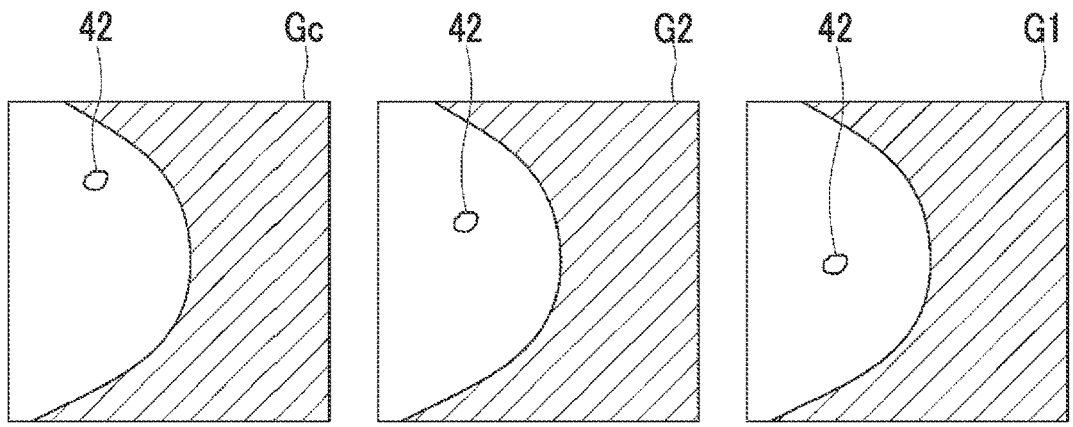
FIG. 8 is a diagram illustrating the position of the lesion image in a first projection image.

In a case in which the lesion image is combined with the first projection image Gi, first, the combination unit 32 derives the combination position of the lesion image with the first projection image Gi on the basis of the geometrical relationship between a plurality of radiation source positions in a case in which the mammography apparatus 1 performs the tomosynthesis imaging and the position of the lesion virtually disposed in the breast M. FIG. 7 is a diagram illustrating the derivation of the combination position of the lesion image in the first embodiment. As illustrated in FIG. 7, it is assumed that a simulated lesion 40 is virtually disposed at a predetermined position in the breast M. As illustrated in FIG. 7, the detection surface 15A of the radiation detector 15 is irradiated with the radiation which has been emitted at each of the radiation source positions S1 to Sn (only S1, S2, and Sc are illustrated in FIG. 7) and transmitted through the simulated lesion 40 in the breast M. In this case, a position on the detection surface 15A of the radiation detector 15 which is irradiated with the radiation transmitted through the simulated lesion 40 differs depending on the radiation source position. Therefore, as illustrated in FIG. 8, the position of a lesion image 42 of the simulated lesion 40 included in the first projection images G1, G2, and Gc acquired at the radiation source positions S1, S2, and Sc differs depending on the radiation source position.

Here, each of the radiation source positions S1 to Sn, the position of the simulated lesion 40 virtually disposed in the breast M, and the position of the detection surface 15A of the radiation detector 15 are known. Therefore, the combination unit 32 derives the combination position of the lesion image 42 with the first projection image Gi from the geometrical relationship among each of the radiation source positions S1 to Sn, the position of the simulated lesion 40 disposed in the breast M, and the position of the detection surface 15A of the radiation detector 15 in a case in which the simulated lesion 40 is virtually disposed in the breast M and the tomosynthesis imaging is performed.

On the other hand, the radiation emitted from the radiation source 16 in a case in which the tomosynthesis imaging is performed is transmitted through the air between the radiation source 16 and the compression plate 17, the compression plate 17, the breast M, and a top plate 13A of the imaging table 13 and is emitted to the radiation detector 15. Therefore, the radiation emitted from the radiation source 16 is attenuated by the air, the compression plate 17, the breast M, and the top plate 13A, is emitted to the radiation detector 15, and is detected as the first projection image Gi.

As described above, in a case in which the simulated lesion 40 is disposed in the breast M and the transmission simulation of the radiation transmitted through the simulated lesion 40 and emitted to the radiation detector 15 is performed, the radiation is transmitted through the air on the compression plate 17, the compression plate 17, the simulated lesion 40, and the top plate 13A of the imaging table 13 and is emitted to the radiation detector 15.

Therefore, in this embodiment, in a case in which the lesion image 42 of the simulated lesion 40 is combined at the combination position of the first projection image Gi, the combination unit 32 derives a radiation attenuation coefficient indicating the attenuation of the radiation transmitted through the simulated lesion 40 and combines the lesion image 42 of the simulated lesion 40 at the combination position of the first projection image Gi on the basis of the radiation attenuation coefficient to derive a second projection image CGi. Hereinafter, the derivation of the radiation attenuation coefficient of the simulated lesion 40 will be described.

In addition, the radiation generation conditions (that is, a target, a filter, and a tube voltage) in a case in which the first projection image Gi is acquired are known and can be acquired from the console 2. In this embodiment, the combination unit 32 acquires an irradiation spectrum P0 of the radiation in a case in which the first projection image Gi is acquired from the radiation generation conditions. Further, in this embodiment, a table that defines the relationship between various radiation generation conditions and the irradiation spectrum P0 is prepared in advance and stored in the storage 23. The combination unit 32 acquires the irradiation spectrum P0 of the radiation in a case in which the first projection image Gi is acquired from the radiation generation conditions acquired from the console 2 with reference to the table stored in the storage 23.

Further, the attenuation of the radiation similarly occurs at any radiation source position Si. Therefore, in this embodiment, hereinafter, it is assumed that the radiation attenuation coefficient of the simulated lesion 40 is derived on the basis of the reference radiation source position Sc. However, the present disclosure is not limited thereto.

Here, the disposition position and size of the simulated lesion 40 in the breast M are known. Therefore, the combination unit 32 derives the path length of the radiation, which has been emitted at the reference radiation source position Sc and incident on the simulated lesion 40, through the simulated lesion 40 as a thickness t1 of the simulated lesion 40.

Further, a radiation attenuation coefficient μl of the simulated lesion 40 for each radiation energy level is known for each type of lesion. Therefore, the combination unit 32 derives a irradiation spectrum P1 after the radiation is transmitted through the simulated lesion 40 from the irradiation spectrum P0, the radiation attenuation coefficient μl of the simulated lesion 40 for each radiation energy level, and the thickness t1 of the simulated lesion 40, using the following Expression (1).

$$P1 = P0 \cdot \exp(-\mu l \cdot t1) \tag{1}$$

Then, the combination unit 32 derives a radiation attenuation coefficient μm of the simulated lesion 40 over the entire energy range of the radiation from the radiation spectrum P0 and the radiation spectrum P1 for each radiation energy level using the following Expression (2).

$$\mu m = -Ln\left(\frac{\int P_1}{\int P_0}\right)/t_1 \tag{2}$$

The combination unit 32 combines the lesion image 42 at the combination position of the first projection image Gi derived as described above, using the radiation attenuation coefficient μm of the simulated lesion 40 derived as described above, to derive the second projection image CGi. Specifically, the pixel value of the projection image CGi at the combination position (x, y) is derived using the following Expression (3) to derive the second projection image CGi. In addition, in Expression (3), G(x, y) is a combination position in the first projection image Gi, CG(x, y) is a combination position in the second projection image CGi, and l(x, y) is the transmission length of the radiation transmitted through the simulated lesion 40 at the combination position (x, y).

$$CG(x,y) = G(x,y) - \mu m \cdot l(x,y) \tag{3}$$

Figure 9:
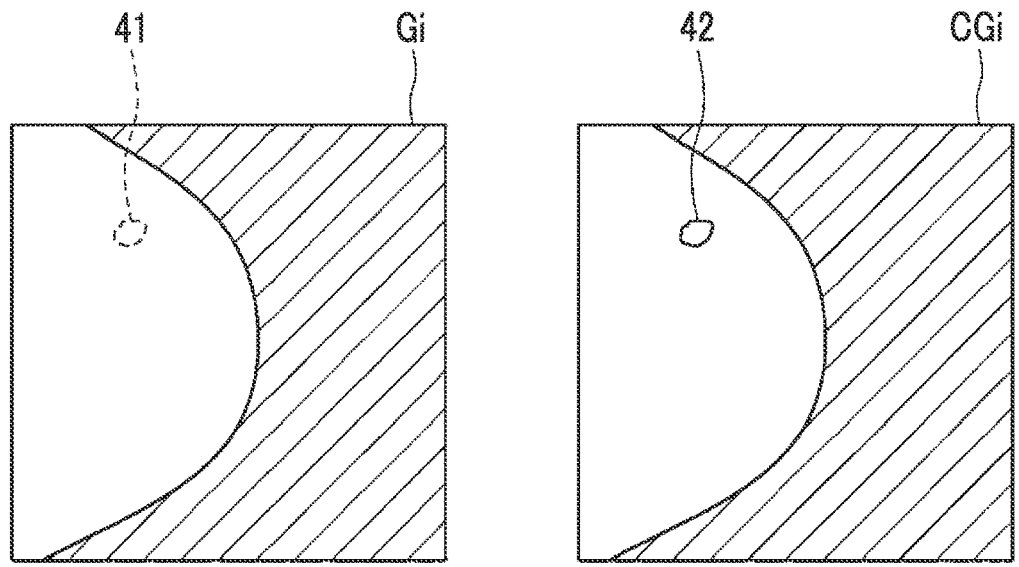
FIG. 9 is a diagram illustrating the first projection image and a second projection image.

FIG. 9 is a diagram illustrating the first projection image Gi and the second projection image CGi. As illustrated in FIG. 9, in the second projection image CGi, the lesion image 42 of the simulated lesion 40 is included at a combination position 41 in the first projection image Gi.

Further, in this embodiment, the combination unit 32 generates the second projection images CGi including the lesion images of various types of simulated lesions having various shapes as illustrated in FIG. 6.

Figure 10:
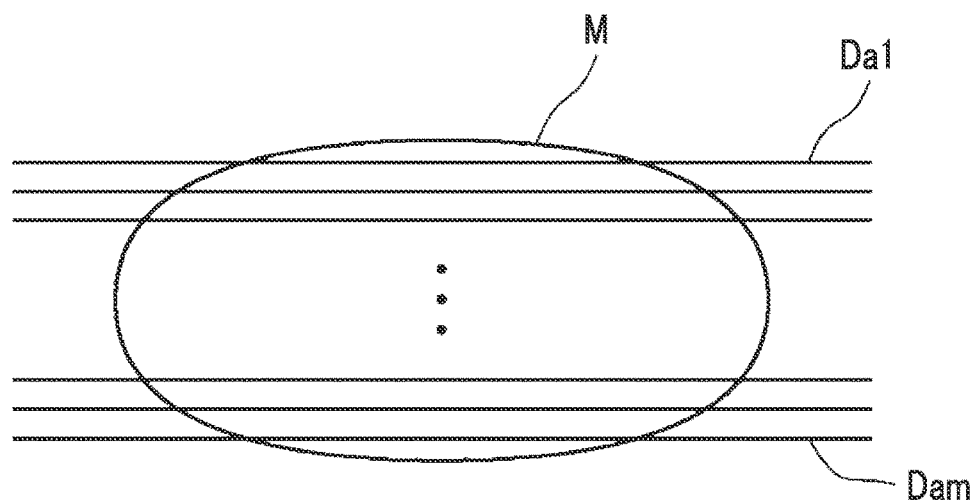
FIG. 10 is a diagram illustrating the generation of first tomographic images.
Figure 11:
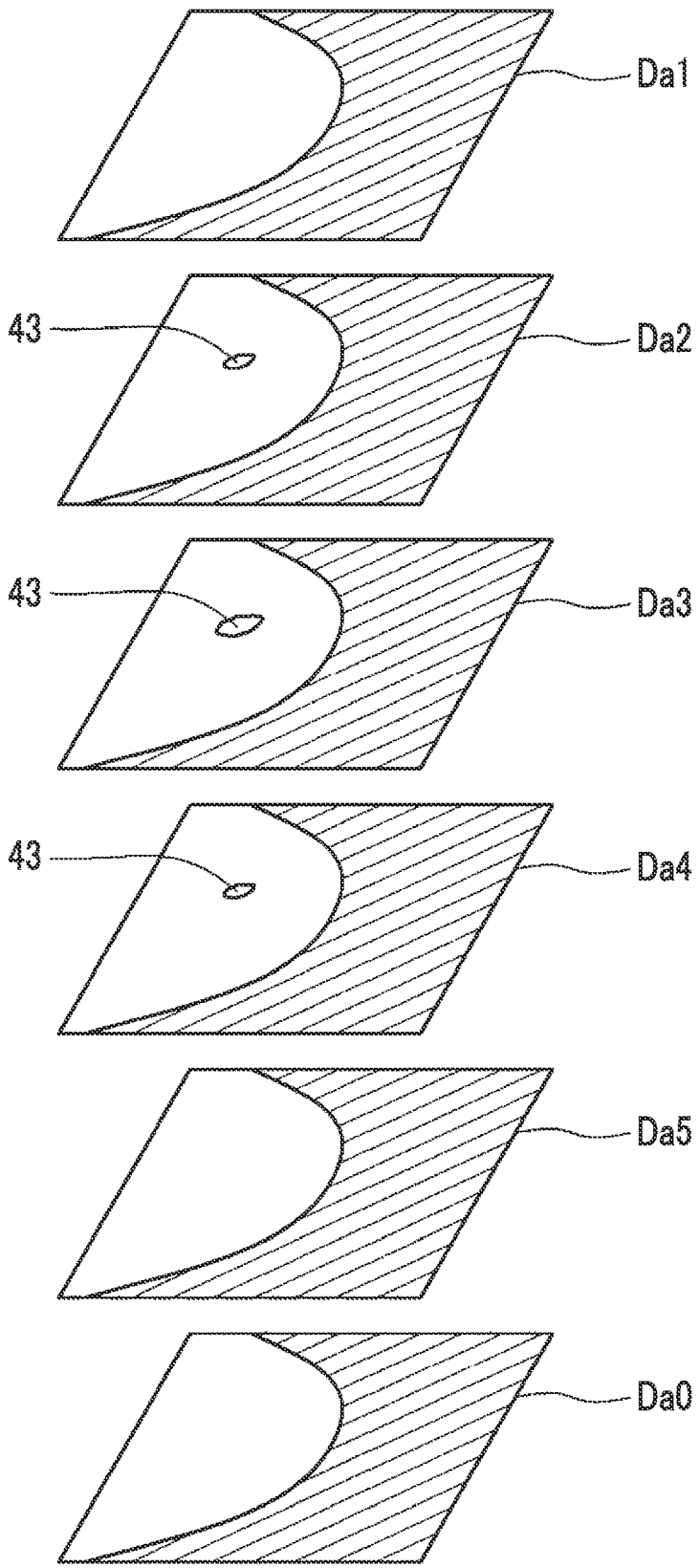
FIG. 11 is a diagram illustrating a tomographic image including a tomographic image of the simulated lesion.

The reconstruction unit 33 reconstructs the second projection images CGi to generate the tomographic images which include the lesion image 42 of the simulated lesion 40 and in which the desired tomographic planes of the breast M have been highlighted. Specifically, the reconstruction unit 33 reconstructs the plurality of second projection images CGi using a known back projection method, such as a simple back projection method or a filtered back projection method, to generate a plurality of tomographic images Daj (j=1 to m) in each of a plurality of tomographic planes of the breast M as illustrated in FIG. 10. In this case, a three-dimensional coordinate position in a three-dimensional space including the breast M is set, pixel values at corresponding pixel positions in the plurality of second projection images CGi are reconstructed for the set three-dimensional coordinate position, and pixel values at the coordinate positions are calculated. In addition, a three-dimensional image of the breast M is constructed by the plurality of tomographic images Daj generated by the reconstruction. Further, as illustrated in FIG. 11, the generated tomographic images Daj include a tomographic image 43 of the simulated lesion 40 virtually disposed in the breast M in a case in which the second projection images CGi are generated. In FIG. 11, the tomographic image 43 of the simulated lesion 40 is included in the tomographic images Da2, Da3, and Da4. In the following description, it is assumed that the tomographic image Daj including the simulated lesion 40 is referred to as an abnormal image. Further, in the following description, it is assumed that the abnormal image is denoted by reference letters Daj.

Figure 12:
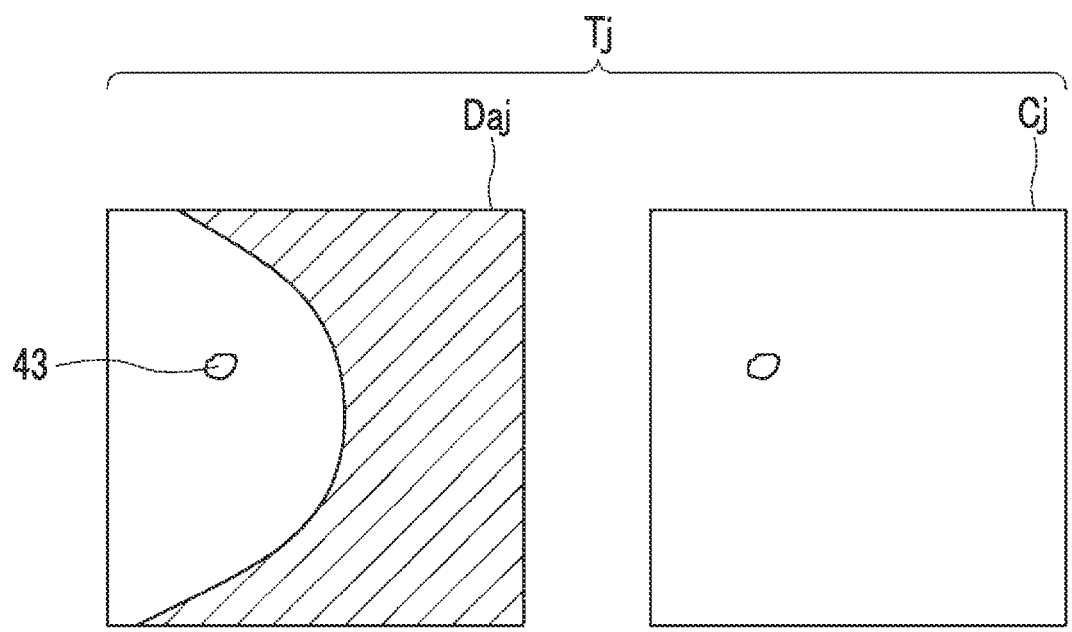
FIG. 12 is a diagram illustrating training data generated in the first embodiment.

The training data generation unit 34 generates training data Tj including the abnormal images (that is, the tomographic images Daj including the tomographic image 43 of the simulated lesion 40) generated as described above and data (hereinafter, referred to as correct answer data) indicating the position of the tomographic image 43 included in each of the abnormal images Daj. FIG. 12 is a diagram schematically illustrating the training data generated in the first embodiment. As illustrated in FIG. 12, the training data Tj consists of the abnormal image Daj including the tomographic image 43 of the simulated lesion 40 and correct answer data Cj indicating the position of the tomographic image 43 of the simulated lesion 40 in the abnormal image Daj. In addition, the training data is generated for each abnormal image Daj. The training data Tj generated by the training data generation unit 34 is stored in the storage 23.

In addition, the display control unit 37 may display the generated abnormal image Daj on the display 24. Further, the communication unit 38 transmits the training data Tj to the image storage system 3. The image storage system 3 stores the received training data Tj.

The learning unit 35 constructs the learning model 36A of the detection unit 36 by training a machine learning model, using the training data Tj for the abnormal image as first training data and training data for a medical image which does not include the lesion as second training data, so as to discriminate a lesion region in the input target image. A plurality of first training data items and a plurality of second training data items are prepared. Therefore, in a case in which the machine learning model is trained, the image acquisition unit 31 acquires the plurality of first training data items and the plurality of second training data items from the storage 23 or the image storage system 3.

An example of the machine learning model for constructing the learning model 36A is a neural network model. Examples of the neural network model include a simple perceptron, a multilayer perceptron, a deep neural network, a convolutional neural network, a deep belief network, a recurrent neural network, and a stochastic neural network. In this embodiment, the convolutional neural network is used as the machine learning model for constructing the learning model 36A.

The learning model 36A is constructed by training the machine learning model so as to output the probability (likelihood) that each pixel of the abnormal image Daj will be the lesion region in a case in which the abnormal image Daj included in the training data is input. A region consisting of the pixels having the probability which has been output from the learning model 36A and is equal to or greater than a predetermined threshold value is the lesion region. The learning unit 35 inputs the abnormal image to the machine learning model and outputs the probability that each pixel of the abnormal image will be the lesion region. Then, the difference between the region consisting of the pixels having the probability which has been output from the machine learning model and is equal to or greater than the predetermined threshold value and the region indicated by the correct answer data included in the training data is derived as a loss. Then, the machine learning model is trained on the basis of the loss. Specifically, for example, a kernel coefficient in the convolutional neural network and a weight for the connection of neural networks are derived so as to reduce the loss. The learning unit 35 repeats the training until the loss is equal to or less than a predetermined threshold value.

Therefore, the learning model 36A is constructed such that the probability higher than the predetermined threshold value is output for the lesion region included in the input target image to extract the lesion region included in the input target image.

The learning model 36A constructed by the learning unit 35 is applied to the detection unit 36. In a case in which the target image is input to the detection unit 36, the detection unit 36 directs the learning model 36A to detect the lesion region included in the target image, thereby detecting the lesion region. In addition, in a case in which the detection unit 36 detects the lesion region from the target image, the image acquisition unit 31 acquires the projection image (referred to as a target projection image), which is to be the target image, from the mammography apparatus 1 or the image storage system 3. Then, the reconstruction unit 33 reconstructs the target projection image to generate a target tomographic image. The detection unit 36 detects the lesion region from the target tomographic image. In addition, the console 2 of the mammography apparatus 1 may generate the target tomographic image from the target projection image. In this case, the image acquisition unit 31 acquires the target tomographic image from the console 2. Further, in a case in which the target tomographic image generated from the target projection image is stored in the image storage system 3, the image acquisition unit 31 may acquire the target tomographic image from the image storage system 3.

Figure 13:
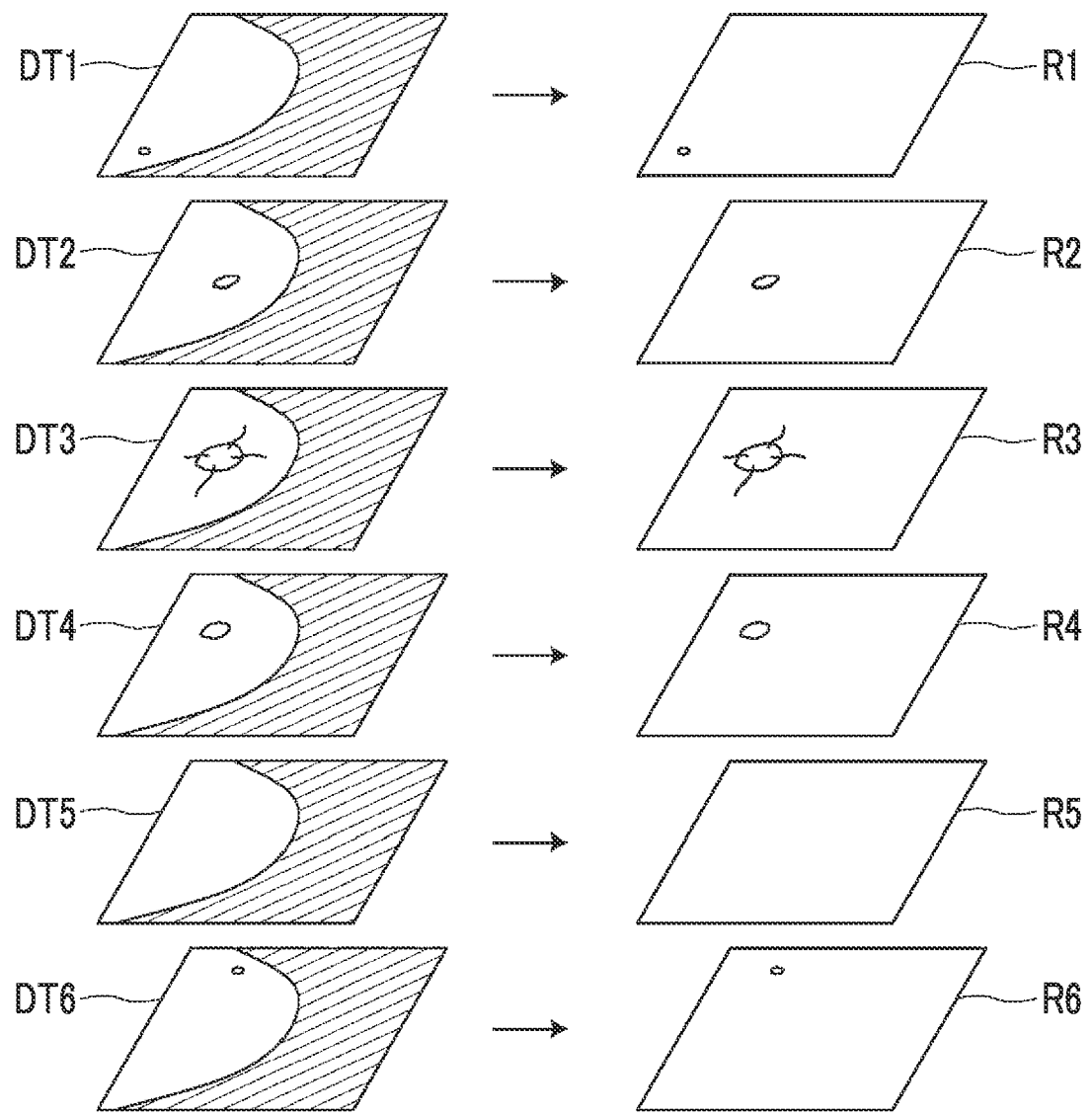
FIG. 13 is a diagram illustrating a target tomographic image and a detection result of a lesion region.

FIG. 13 is a diagram illustrating the target tomographic images and the detection result of the lesion region. As illustrated in FIG. 13, for example, the detection unit 36 detects the lesion region from six target tomographic images DT1 to DT6 and outputs detection results R1 to R6.

Figure 14:
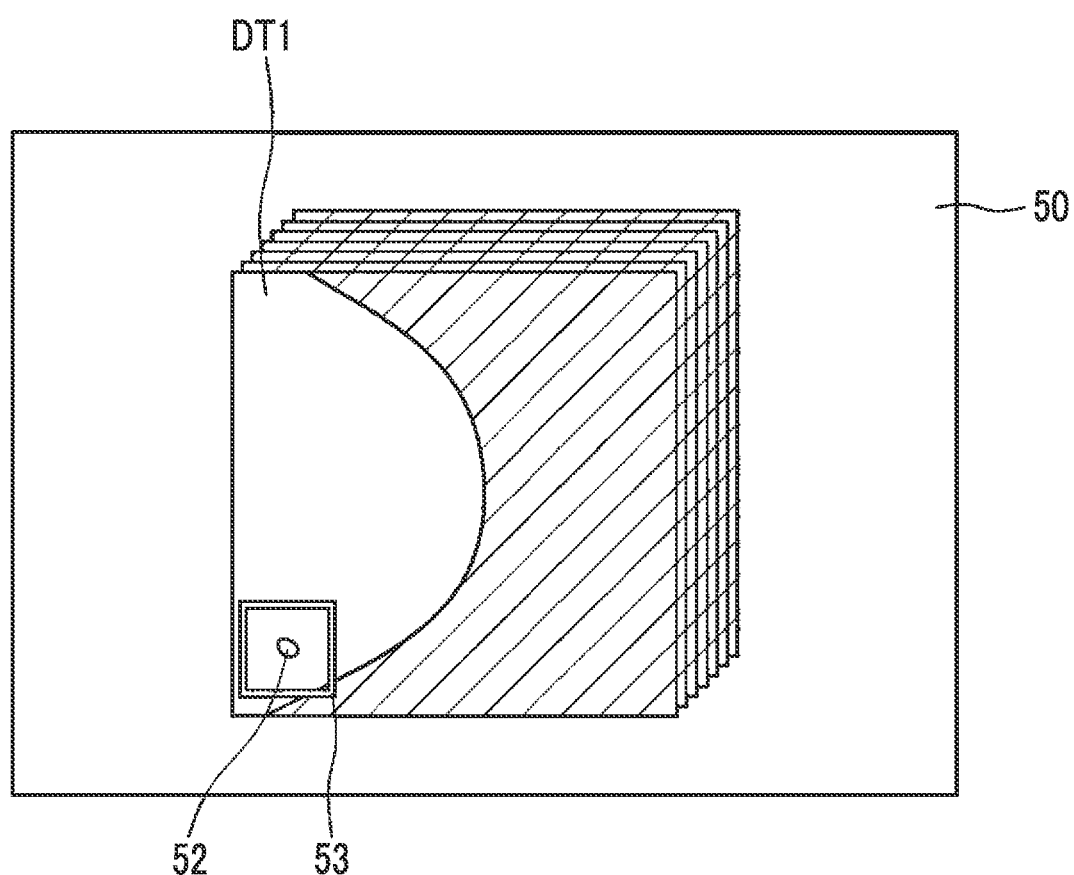
FIG. 14 is a diagram illustrating a display screen for the detection result of the target tomographic image in the first embodiment.

The display control unit 37 displays the target tomographic image on the display 24 such that the lesion region detected from the target tomographic image by the detection unit 36 is highlighted. FIG. 14 is a diagram illustrating a display screen for the detection result of the target tomographic image in the first embodiment. As illustrated in FIG. 14, the first target tomographic image DT1 among the six target tomographic images DT1 to DT6 illustrated in FIG. 13 is displayed on a display screen 50. The displayed target tomographic image can be switched by an operation through the input device 25. The display control unit 37 surrounds a lesion region 52 included in the target tomographic image DT1 with a rectangular frame 53 to highlight the lesion region 52 in the target tomographic image DT1. In addition, the rectangular frame 53 is illustrated in white in FIG. 14. However, the rectangular frame 53 may be colored. Further, instead of giving the rectangular frame 53, a mark, such as an arrow or an asterisk, may be given in the vicinity of the lesion region to highlight the lesion region.

Figure 15:
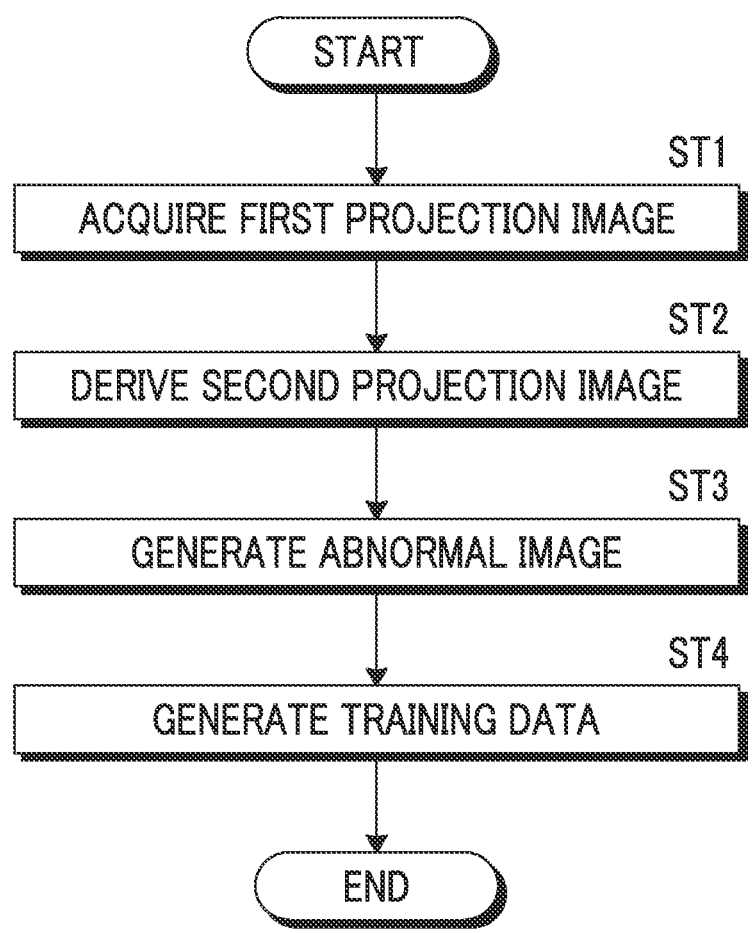
FIG. 15 is a flowchart illustrating an image generation process performed in the first embodiment.

Next, a process performed in the first embodiment will be described. FIG. 15 is a flowchart illustrating an image generation process performed in the first embodiment. First, the image acquisition unit 31 acquires a plurality of first projection images Gi (Step ST1). Then, the combination unit 32 combines the lesion image 42 with the first projection images Gi on the basis of the geometrical relationship between a plurality of radiation source positions in a case in which the mammography apparatus 1 performs the tomosynthesis imaging and the position of the simulated lesion virtually disposed in the breast M to derive a plurality of second projection images CGi (Step ST2).

Then, the reconstruction unit 33 reconstructs the plurality of second projection images CGi to generate, as the abnormal images Daj, the tomographic images which include the tomographic image 43 of the simulated lesion 40 and in which a desired tomographic plane of the breast M has been highlighted (abnormal image generation: Step ST3). Then, the training data generation unit 34 generates the training data Tj including the abnormal images Daj generated as described above and the correct answer data Cj indicating the position of the tomographic image 43 of the simulated lesion 40 included in each of the abnormal images Daj (Step ST4). Then, the process ends. The generated training data Tj is stored in the storage 23 and is further transmitted to the image storage system 3 by the communication unit 38.

Figure 16:
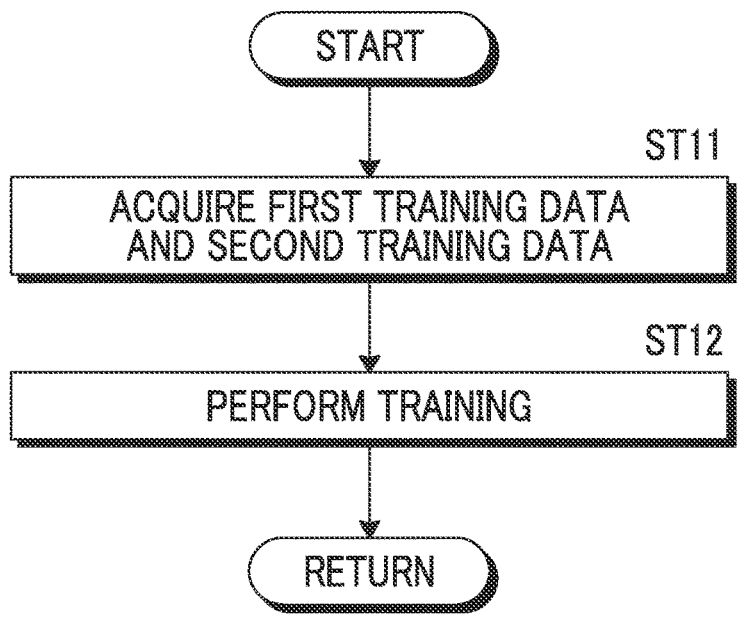
FIG. 16 is a flowchart illustrating a learning process performed in the first embodiment.

Next, a learning process according to the first embodiment will be described. FIG. 16 is a flowchart illustrating the learning process performed in the first embodiment. First, the image acquisition unit 31 acquires the first training data and the second training data (Step ST11). The learning unit 35 inputs the first training data and the second training data to the machine learning model for constructing the learning model 36A of the detection unit 36 to acquire the extraction result of the lesion region, trains the machine learning model using the loss based on a difference from the correct answer data (Step ST12), and returns to Step ST11. Then, the learning unit 35 repeats the processes in Steps ST11 and ST12 until the loss reaches a predetermined threshold value and ends the training of the machine learning model. In this way, the learning model 36A is constructed. In addition, the learning unit 35 may repeat the training a predetermined number of times and end the training.

Figure 17:
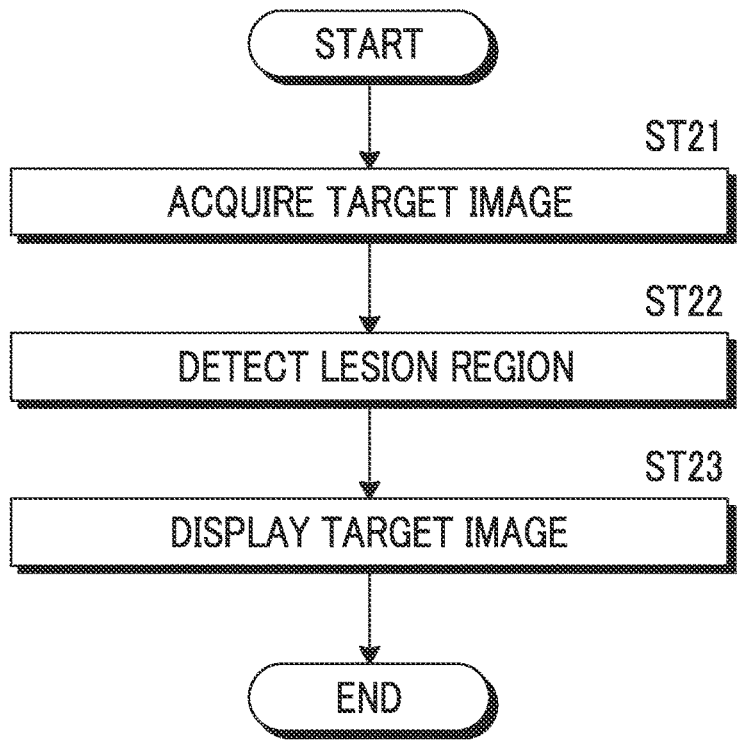
FIG. 17 is a flowchart illustrating a detection process performed in the first embodiment.

Next, a lesion region detection process according to the first embodiment will be described. FIG. 17 is a flowchart illustrating the detection process performed in the first embodiment. The image acquisition unit 31 acquires the target image (target tomographic image DTj) to be detected (Step ST21), and the detection unit 36 detects the lesion region from the target image (Step ST22). Then, the display control unit 37 displays the target image in which the lesion region has been highlighted on the display 24 (Step ST23). Then, the process ends.

Here, it is difficult to collect a large number of abnormal images including lesions which are necessary for training the machine learning model for constructing the learning model 36A. In this embodiment, the tomographic images Daj including the tomographic image 43 of the simulated lesion 40 are generated as the abnormal images, using the second projection images CGi generated by combining the lesion image 42 of the simulated lesion 40 with the first projection images Gi. Therefore, the tomographic images including various types of lesions at various positions can be generated as the abnormal images by changing the type of simulated lesion 40 in various ways or by changing the position where the simulated lesion 40 is provided in various ways. As a result, it is possible to prepare a sufficient number of abnormal images and sufficient variations of abnormal images in order to train the machine learning model for constructing the learning model 36A.

Further, the learning model 36A for discriminating the lesion region from the input target image is constructed by machine learning, using the first training data consisting of the abnormal image and data including information indicating the position of the lesion image in the abnormal image. Here, in this embodiment, it is possible to prepare a sufficient number of abnormal images, sufficient variations of abnormal images, and the first training data in order to train the machine learning model for constructing the learning model 36A. Therefore, according to this embodiment, it is possible to construct the learning model 36A having high lesion detection accuracy.

Further, since the second projection images CGi are derived on the basis of the radiation attenuation coefficient μm of the simulated lesion 40, it is possible to acquire the second projection images CGi as in a case in which the breast M including the lesion is actually imaged. Therefore, it is possible to construct the learning model 36A having high lesion detection accuracy.

Next, a second embodiment of the present disclosure will be described. In addition, the configuration of an image processing device according to the second embodiment is the same as the configuration of the image processing device 4 according to the first embodiment except only the process to be performed. Therefore, the detailed description of the device will not be repeated here. In the first embodiment, the lesion image 42 of the simulated lesion 40 is combined with the first projection image Gi acquired by the tomosynthesis imaging to generate the second projection image CGi, and the tomographic image is generated as the abnormal image from the second projection image CGi. The second embodiment differs from the first embodiment in that an image obtained by combining the lesion image 42 of the simulated lesion 40 with a radiographic image acquired by simple imaging is generated as the abnormal image.

In addition, the image processing device according to the second embodiment does not require the reconstruction unit 33 according to the first embodiment. Therefore, the image processing device according to the second embodiment may not comprise the reconstruction unit 33.

In the second embodiment, the mammography apparatus 1 performs the simple imaging which irradiates the breast M with radiation only at the reference radiation source position Sc to acquire a radiographic image H0 of the breast M. The image acquisition unit 31 acquires the radiographic image H0 of the breast M obtained by the simple imaging.

Figure 18:
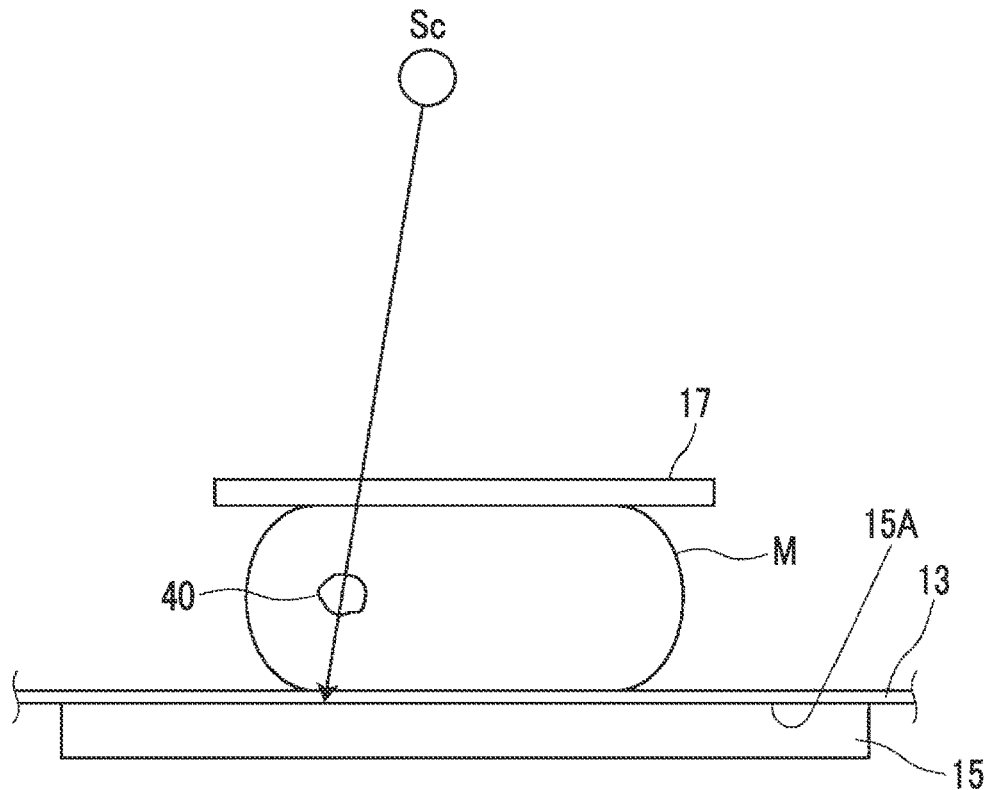
FIG. 18 is a diagram illustrating the derivation of a combination position of a lesion image in a second embodiment.

The combination unit 32 combines the lesion image 42 of the simulated lesion 40 at a combination position of the radiographic image H0. FIG. 18 is a diagram illustrating the combination position of the lesion image 42 of the simulated lesion 40 in the second embodiment. In the second embodiment, the breast M is imaged only at the reference radiation source position Sc. Therefore, the combination unit 32 derives the combination position of the lesion image 42 in the radiographic image H0 on the basis of a geometrical relationship among the reference radiation source position Sc, the position of the simulated lesion 40 virtually disposed in the breast M, and the position of the detection surface 15A of the radiation detector 15.

Then, as in the first embodiment, the combination unit 32 performs the radiation attenuation simulation to derive the radiation attenuation coefficient μm of the simulated lesion 40 and combines the lesion image 42 at the combination position in the radiographic image H0 derived as described above, using the radiation attenuation coefficient μm, to generate an abnormal image H1.

Figure 19:
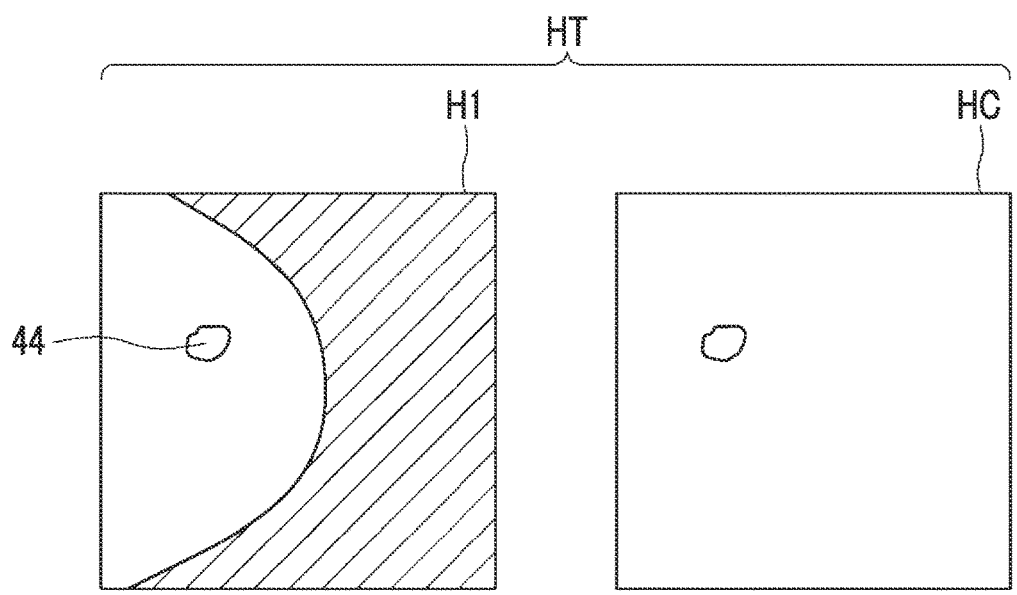
FIG. 19 is a diagram illustrating training data generated in the second embodiment.

The training data generation unit 34 generates training data HT including the abnormal image H1 generated as described above and data (correct answer data) indicating the position of the lesion image included in the abnormal image H1. FIG. 19 is a diagram schematically illustrating the training data generated in the second embodiment. As illustrated in FIG. 19, the training data HT consists of the abnormal image H1 including the lesion image 44 of the simulated lesion 40 and correct answer data HC indicating the position of the lesion image 44 of the simulated lesion 40 in the abnormal image H1. The training data HT generated by the training data generation unit 34 is stored in the storage 23.

In addition, the display control unit 37 may be configured to display the generated abnormal image H1 on the display 24. Further, the communication unit 38 transmits the training data HT to the image storage system 3. The image storage system 3 stores the received training data HT.

Further, in the second embodiment, the learning unit 35 trains the machine learning model so as to discriminate the lesion region in the input target image acquired by the simple imaging, using the training data HT for the abnormal image H1 as the first training data and training data for the medical image, which does not include the lesion, as the second training data, to construct the learning model 36A of the detection unit 36. A plurality of first training data items and a plurality of second training data items are prepared. Therefore, in a case in which the machine learning model is trained, the image acquisition unit 31 acquires the plurality of first training data items and the plurality of second training data items from the storage 23 or the image storage system 3. In addition, since the learning process performed by the learning unit 35 is the same as that in the first embodiment except that the training data is a tomographic image, the detailed description thereof will not be repeated here.

In the second embodiment, in a case in which the target image acquired by the simple imaging is input, the detection unit 36 directs the learning model 36A to detect the lesion region included in the target image, thereby detecting the lesion region.

Figure 20:
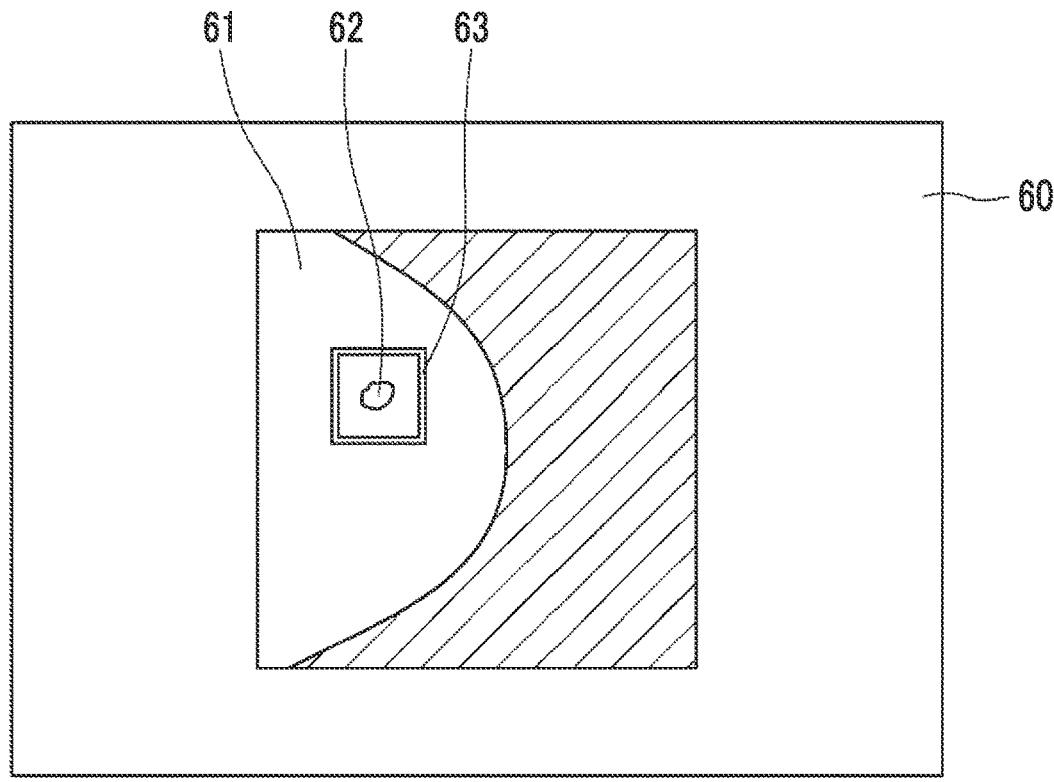
FIG. 20 is a diagram illustrating a display screen for a detection result of a target image in the second embodiment.

In the second embodiment, the display control unit 37 displays the target image on the display 24 such that the lesion region detected by the detection unit 36 from the target image is highlighted. FIG. 20 is a diagram illustrating a display screen for the detection result of the target image in the second embodiment. As illustrated in FIG. 20, a target image 61 is displayed on a display screen 60. The display control unit 37 surrounds a lesion region 62 included in the target image 61 with a rectangular frame 63 to highlight the lesion region 62 in the target image 61.

Figure 21:
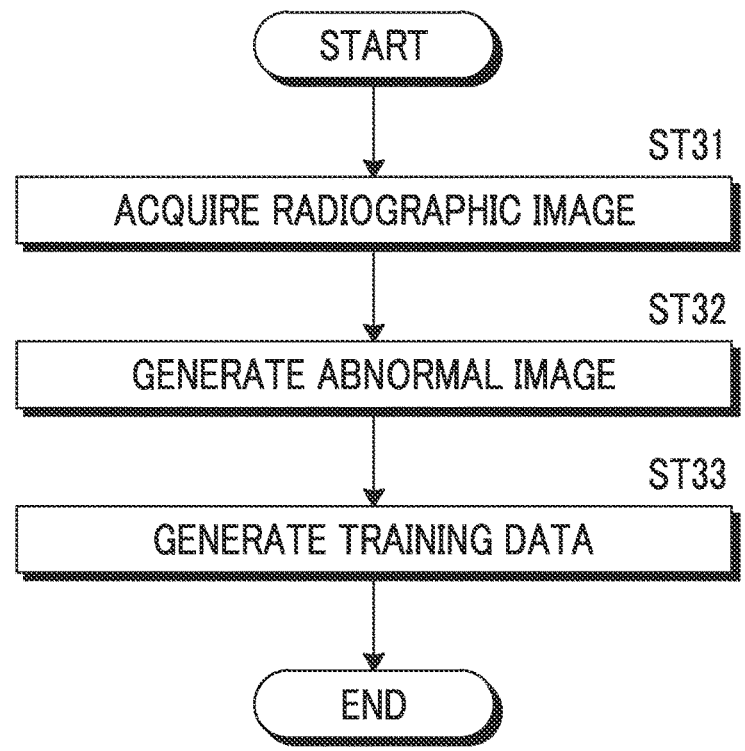
FIG. 21 is a flowchart illustrating an image generation process performed in the second embodiment.

Next, a process performed in the second embodiment will be described. FIG. 21 is a flowchart illustrating an image generation process performed in the second embodiment. First, the image acquisition unit 31 acquires the radiographic image H0 for generating an abnormal image (Step ST31). Then, the combination unit 32 combines the lesion image with the radiographic image H0 on the basis of the geometrical relationship between the radiation source position in a case in which the mammography apparatus 1 performs imaging and the position of the simulated lesion virtually disposed in the breast M to generate the abnormal image H1 (Step ST32).

Then, the training data generation unit 34 generates training data including the abnormal image H1 and correct answer data indicating the position of the lesion image included in the abnormal image H1 (Step ST33). Then, the process ends. The generated training data is stored in the storage 23 and is further transmitted to the image storage system 3 by the communication unit 38.

In addition, the learning process in the second embodiment is the same as that in the first embodiment except that the training data consists of the abnormal image H1 and the correct answer data. Further, the lesion detection process in the second embodiment is the same as that in the first embodiment except that the target image is a radiographic image acquired by the simple imaging. Therefore, the detailed description of the learning process and the lesion detection process in the second embodiment will not be repeated.

Furthermore, in the first embodiment, the lesion image 42 of the simulated lesion 40 is combined with a plurality of tomographic images to generate the abnormal images Daj including the tomographic image 43 of the simulated lesion 40. Therefore, a composite two-dimensional image may be generated using a plurality of abnormal images Daj. The composite two-dimensional image is a pseudo two-dimensional image equivalent to a simple two-dimensional image obtained by combining a plurality of tomographic images including the abnormal image using, for example, an addition method, an averaging method, a maximum intensity projection method, or a minimum intensity projection method (see JP2014-128716A).

FIG. 22 is a diagram illustrating the generation of the composite two-dimensional image. In addition, the combination unit 32 may generate the composite two-dimensional image, or a composite two-dimensional image generation unit for generating the composite two-dimensional image may be provided and generate the composite two-dimensional image. As illustrated in FIG. 22, the combination unit 32 generates a composite two-dimensional image GG0 by combining the pixel values of the corresponding pixel positions of a plurality of tomographic images including the abnormal images along a viewing direction from the reference radiation source position Sc to the radiation detector 15, that is, along the optical axis X0 illustrated in FIG. 5 in a state in which a plurality of abnormal images Daj are stacked.

In a case in which the composite two-dimensional image GG0 is generated in this way, the training data generation unit 34 generates training data from the composite two-dimensional image GG0 and data indicating the position of the lesion image of the simulated lesion 40 included in the composite two-dimensional image GG0. The learning unit 35 constructs the learning model 36A of the detection unit 36 by training the machine learning model using the training data so as to detect the lesion included in the composite two-dimensional image in a case in which the composite two-dimensional image is input. The use of the learning model 36A constructed in this way makes it possible to detect the lesion from the target image which is the composite two-dimensional image in a case in which the composite two-dimensional image is input as the target image to the detection unit 36.

In addition, a method for generating the composite two-dimensional image is not limited to the above-mentioned method. For example, as in the method disclosed in U.S. Pat. No. 8,983,156B, only the tomographic images included in the abnormal images Daj may be combined with any tomographic image prepared in advance to generate the composite two-dimensional image. Further, as described in U.S. Pat. No. 9,792,703B, only the tomographic images included in the abnormal images Daj may be averaged and combined to generate the composite two-dimensional image.

Furthermore, the radiation in the above-described embodiments is not particularly limited. For example, α-rays or γ-rays can be applied in addition to the X-rays.

Moreover, in each of the above-described embodiments, the object is the breast M. However, the object is not limited thereto. In addition to the breast M, any part of the human body, such as the heart, the liver, the brain, and the limbs, can be used as the object. In this case, the simulated lesion corresponding to the type of object may be prepared. In addition, the learning model 36A of the detection unit 36 which detects a lesion corresponding to the object is prepared and trained using the generated training data including the abnormal image. The detection unit 36 detects the lesion corresponding to the object.

Further, in the above-described embodiments, for example, the following various processors can be used as a hardware structure of processing units performing various processes, such as the image acquisition unit 31, the combination unit 32, the reconstruction unit 33, the training data generation unit 34, the learning unit 35, the detection unit 36, the display control unit 37, and the communication unit 38. The various processors include, for example, a CPU which is a general-purpose processor executing software (program) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

What is claimed is:

1. An image generation device comprising at least one processor,
    wherein the processor is configured to:
    acquire a plurality of first projection images acquired by imaging an object at a plurality of radiation source positions;
    acquire a lesion image indicating a lesion;
    obtain a first radiation spectrum used when the object is radiographically imaged, based on radiation emission conditions and a thickness of the object;
    derive a radiation attenuation coefficient for the lesion virtually disposed in the object, based on the first radiation spectrum and a second radiation spectrum after transmission through the lesion virtually disposed in the object;
    combine the lesion image with the plurality of first projection images on the basis of the radiation attenuation coefficient and a geometrical relationship between the plurality of radiation source positions and a position of the lesion virtually disposed in the object to derive a plurality of second projection images; and
    reconstruct the plurality of second projection images to generate a tomographic image including the lesion.

2. The image generation device according to claim 1,
    wherein the processor generates training data that includes the tomographic image including the lesion and data indicating a position of the lesion in the tomographic image including the lesion and that is used to perform machine learning on a model for detecting the lesion included in a target image in a case in which the target image is input.

3. The image generation device according to any claim 1,
    wherein the lesion is at least one of a tumor, a spicula, or a calcification.

4. An image generation device comprising at least one processor,
    wherein the processor is configured to;
    acquire an image acquired by performing radiography on an object;
    acquire a lesion image indicating a lesion;
    obtain a first radiation spectrum used when the object is radiographically imaged, based on radiation emission conditions and a thickness of the object;
    derive a radiation attenuation coefficient for the lesion virtually disposed in the object, based on the first radiation spectrum and a second radiation spectrum after transmission through the lesion virtually disposed in the object; and
    combine the lesion image with the image on the basis of the radiation attenuation coefficient and a geometrical relationship between a radiation source position in a case in which the radiography is performed and a position of the lesion virtually disposed in the object to generate an image.

5. The image generation device according to claim 4,
    wherein the processor generates training data that includes the image in which with the lesion image has been combined and data indicating a position of the lesion in the image in which the lesion image has been combined and that is used to perform machine learning on a model for detecting the lesion included in a target image in a case in which the target image is input.

6. A learning device comprising at least one processor,
    wherein the processor is configured to construct a model, which detects a lesion included in a target image in a case in which the target image is input, with machine learning, using first training data which is the training data generated by the image generation device according to claim 2 and second training data which is an image that does not include the lesion.

7. An image processing device comprising:
    at least one processor; and
    the model constructed by the learning device according to claim 6,
    wherein the processor is configured to;
    acquire a target image; and
    detect a lesion included in the target image using the model.

8. The image processing device according to claim 7,
    wherein the processor is configured to display a detection result of the lesion.

9. A learning device comprising at least one processor,
    wherein the processor is configured to construct a model, which detects a lesion included in a target image in a case in which the target image is input, with machine learning, using first training data which is the training data generated by the image generation device according to claim 5 and second training data which is an image that does not include the lesion.

10. An image processing device comprising:
at least one processor; and
the model constructed by the learning device according to claim 9,
wherein the processor is configured to;
acquire a target image; and
detect a lesion included in the target image using the model.

11. The image processing device according to claim 10, wherein the processor is configured to display a detection result of the lesion.

12. A non-transitory computer-readable storage medium that stores an image generation program that causes a computer to execute:
a procedure of acquiring a plurality of first projection images acquired by imaging an object at a plurality of radiation source positions;
a procedure of acquiring a lesion image indicating a lesion;
a procedure of obtaining a first radiation spectrum used when the object is radiographically imaged, based on radiation emission conditions and a thickness of the object;
a procedure of deriving a radiation attenuation coefficient for the lesion virtually disposed in the object, based on the first radiation spectrum and a second radiation spectrum after transmission through the lesion virtually disposed in the object;
a procedure of combining the lesion image with the plurality of first projection images on the basis of the radiation attenuation coefficient and a geometrical relationship between the plurality of radiation source positions and a position of the lesion virtually disposed in the object to derive a plurality of second projection images; and
a procedure of reconstructing the plurality of second projection images to generate a tomographic image including the lesion.

13. A non-transitory computer-readable storage medium that stores an image generation program that causes a computer to execute:
a procedure of acquiring an image acquired by performing radiography on an object;
a procedure of acquiring a lesion image indicating a lesion;
a procedure of obtaining a first radiation spectrum used when the object is radiographically imaged, based on radiation emission conditions and a thickness of the object;
a procedure of deriving a radiation attenuation coefficient for the lesion virtually disposed in the object, based on the first radiation spectrum and a second radiation spectrum after transmission through the lesion virtually disposed in the object; and
a procedure of combining the lesion image with the image on the basis of the radiation attenuation coefficient and a geometrical relationship between a radiation source position in a case in which the radiography is performed and a position of the lesion virtually disposed in the object to generate an image.

14. A non-transitory computer-readable storage medium that stores a learning program that causes a computer to execute a procedure of constructing a model, which detects a lesion included in a target image in a case in which the target image is input, with machine learning, using first training data which is the training data generated by the image generation device according to claim 2 and second training data which is an image that does not include the lesion.

15. A non-transitory computer-readable storage medium that stores a learning program that causes a computer to execute a procedure of constructing a model, which detects a lesion included in a target image in a case in which the target image is input, with machine learning, using first training data which is the training data generated by the image generation device according to claim 5 and second training data which is an image that does not include the lesion.

16. A non-transitory computer-readable storage medium that stores an image processing program that causes a computer to execute:
a procedure of acquiring a target image; and
a procedure of detecting a lesion included in the target image using the model constructed by the learning device according to claim 6.

17. A non-transitory computer-readable storage medium that stores an image processing program that causes a computer to execute:
a procedure of acquiring a target image; and
a procedure of detecting a lesion included in the target image using the model constructed by the learning device according to claim 9.

* * * * *